United States Patent
Daly et al.

(10) Patent No.: US 10,932,829 B2
(45) Date of Patent: Mar. 2, 2021

(54) INTRAMEDULLARY NAIL SYSTEM

(71) Applicant: Orthoxel Dac, Cork (IE)

(72) Inventors: Charles Daly, County Cork (IE);
Hannah Dailey, Neshanic Station, NJ (US); James Harty, County Cork (IE);
Aidan Connolly, County Galway (IE);
John Eastwood, County Galway (IE)

(73) Assignee: Orthoxel DAC, Cork (IE)

( * ) Notice: Subject to any disclaimer, the term of this patent is extended or adjusted under 35 U.S.C. 154(b) by 169 days.

(21) Appl. No.: 16/092,399

(22) PCT Filed: Apr. 7, 2017

(86) PCT No.: PCT/EP2017/058343
§ 371 (c)(1),
(2) Date: Oct. 9, 2018

(87) PCT Pub. No.: WO2017/178354
PCT Pub. Date: Oct. 19, 2017

(65) Prior Publication Data
US 2020/0323568 A1    Oct. 15, 2020

Related U.S. Application Data

(60) Provisional application No. 62/322,711, filed on Apr. 14, 2016.

(30) Foreign Application Priority Data

Apr. 14, 2016   (EP) .................................... 16165436

(51) Int. Cl.
*A61B 17/72*    (2006.01)

(52) U.S. Cl.
CPC ...... *A61B 17/7233* (2013.01); *A61B 17/7241* (2013.01)

(58) Field of Classification Search
CPC .............. A61B 17/725; A61B 17/7241; A61B 17/7225; A61B 17/7216; A61B 17/72;
(Continued)

(56) References Cited

U.S. PATENT DOCUMENTS 9,308,031 B2 *   4/2016   Elghazaly .......... A61B 17/7241
2002/0151898 A1 *  10/2002  Sohngen ............ A61B 17/7233
                                                            606/62

(Continued)

FOREIGN PATENT DOCUMENTS

| WO | WO-2001/043652 A1 | 6/2001 |
| WO | WO-2011/018778 A1 | 2/2011 |
| WO | WO-2016/030360 A1 | 3/2016 |

*Primary Examiner* — Pedro Philogene
(74) *Attorney, Agent, or Firm* — Cesari and McKenna, LLP

(57) ABSTRACT

An intramedullary nail system (1) comprising a nail stem (2) having a multi-featured proximal end (3), a distal end (5) and a central conduit (22) configured to accommodate a fastener (4) having a proximal end (7), a distal end (9) and a central shaft (22*a*), wherein the fastener (4) comprises a stop (8) extending laterally from the proximal end (7) relative to a vertical axis of the fastener (4) and which is configured to matingly engage with an internal wall (3*a*) of the multi-featured proximal end (3) to provide control over rotational and distal movement of the system (1) when secured with a bone screw.

17 Claims, 20 Drawing Sheets

(58) Field of Classification Search
CPC ............ A61B 17/7233; A61B 17/7283; A61B 17/744; A61B 17/1725; A61B 17/1775; A61B 17/921
USPC .................. 606/62–68, 95, 96, 105, 301
See application file for complete search history.

(56) References Cited

U.S. PATENT DOCUMENTS

| | | | |
|---|---|---|---|
| 2005/0203510 A1* | 9/2005 | Sohngen | A61B 17/744 606/60 |
| 2008/0183171 A1* | 7/2008 | Elghazaly | A61B 17/7241 606/64 |
| 2008/0294164 A1* | 11/2008 | Frank | A61B 17/7241 606/64 |

* cited by examiner

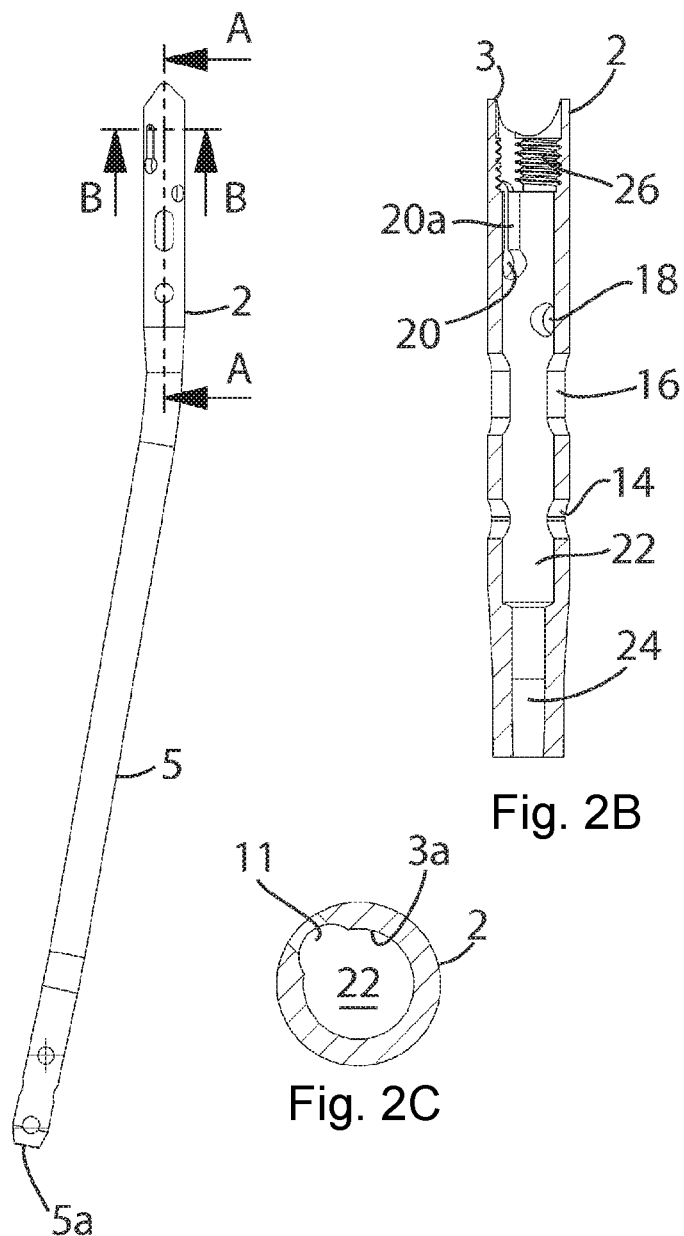

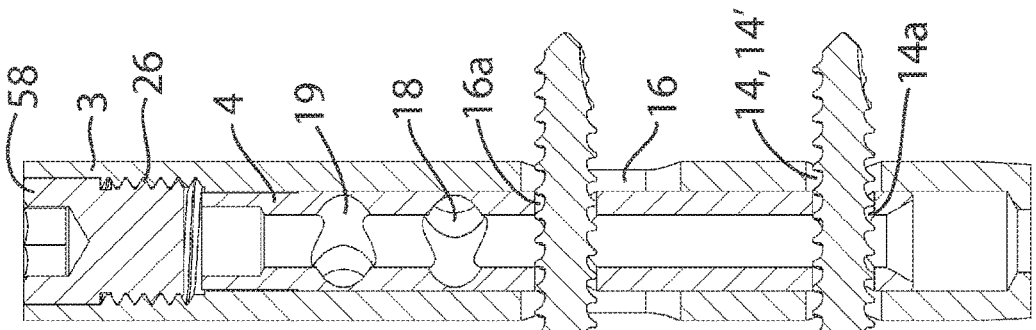
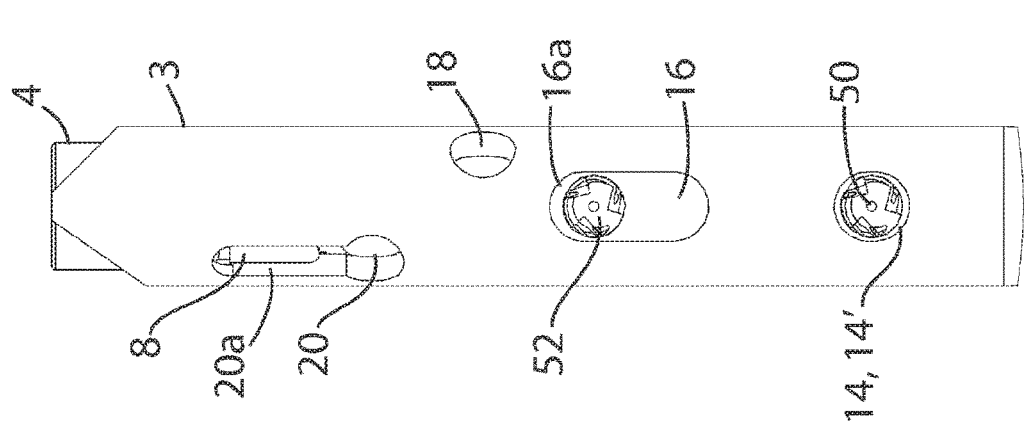
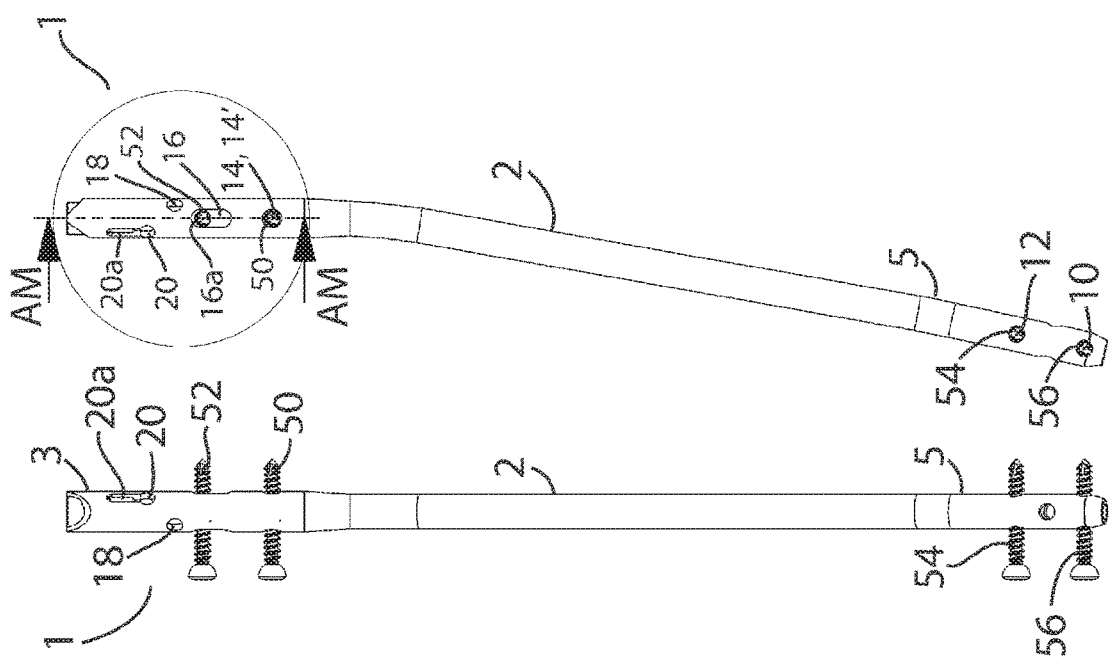
Fig. 7A  Fig. 7B  Fig. 7C  Fig. 7D

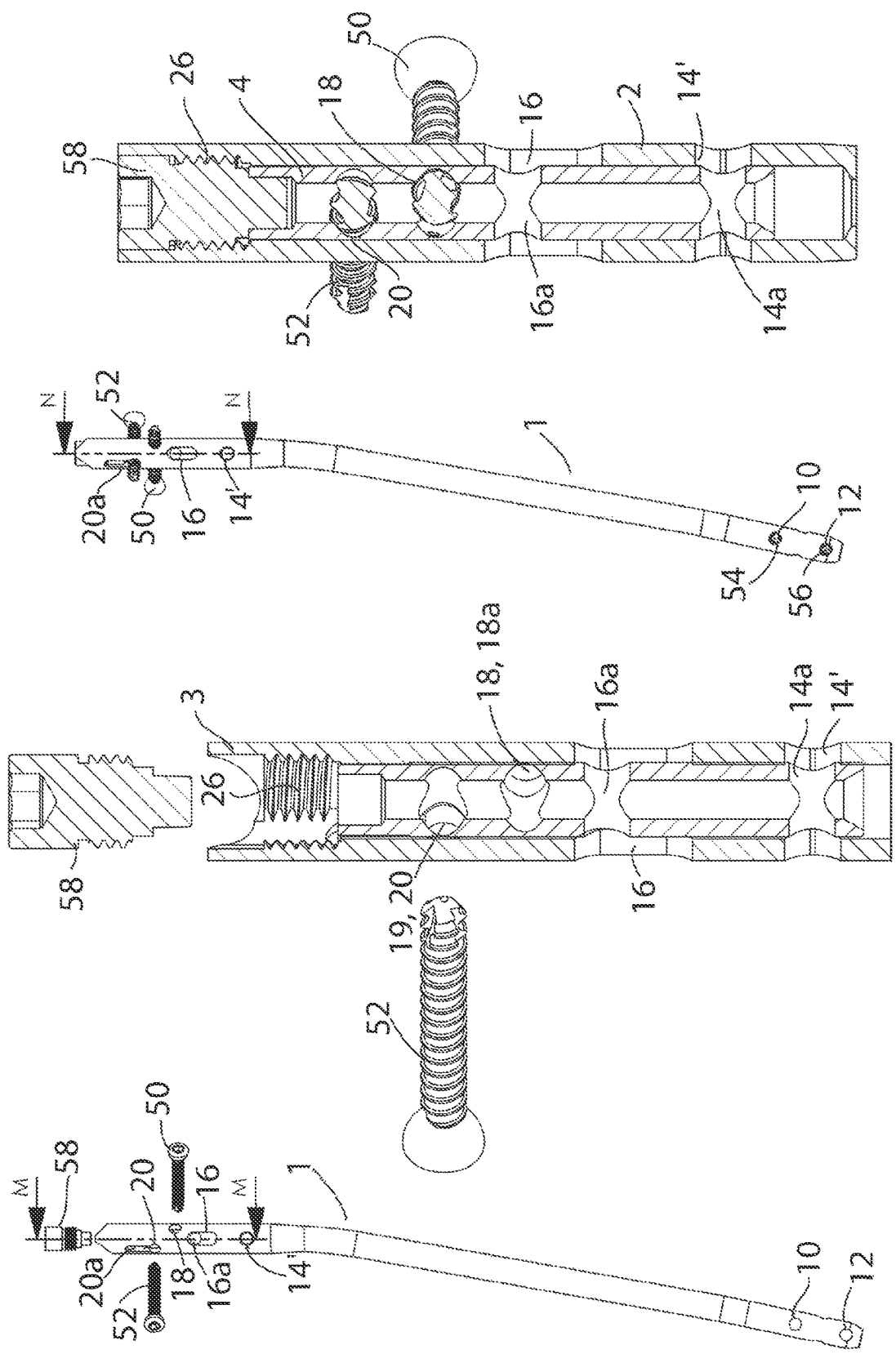

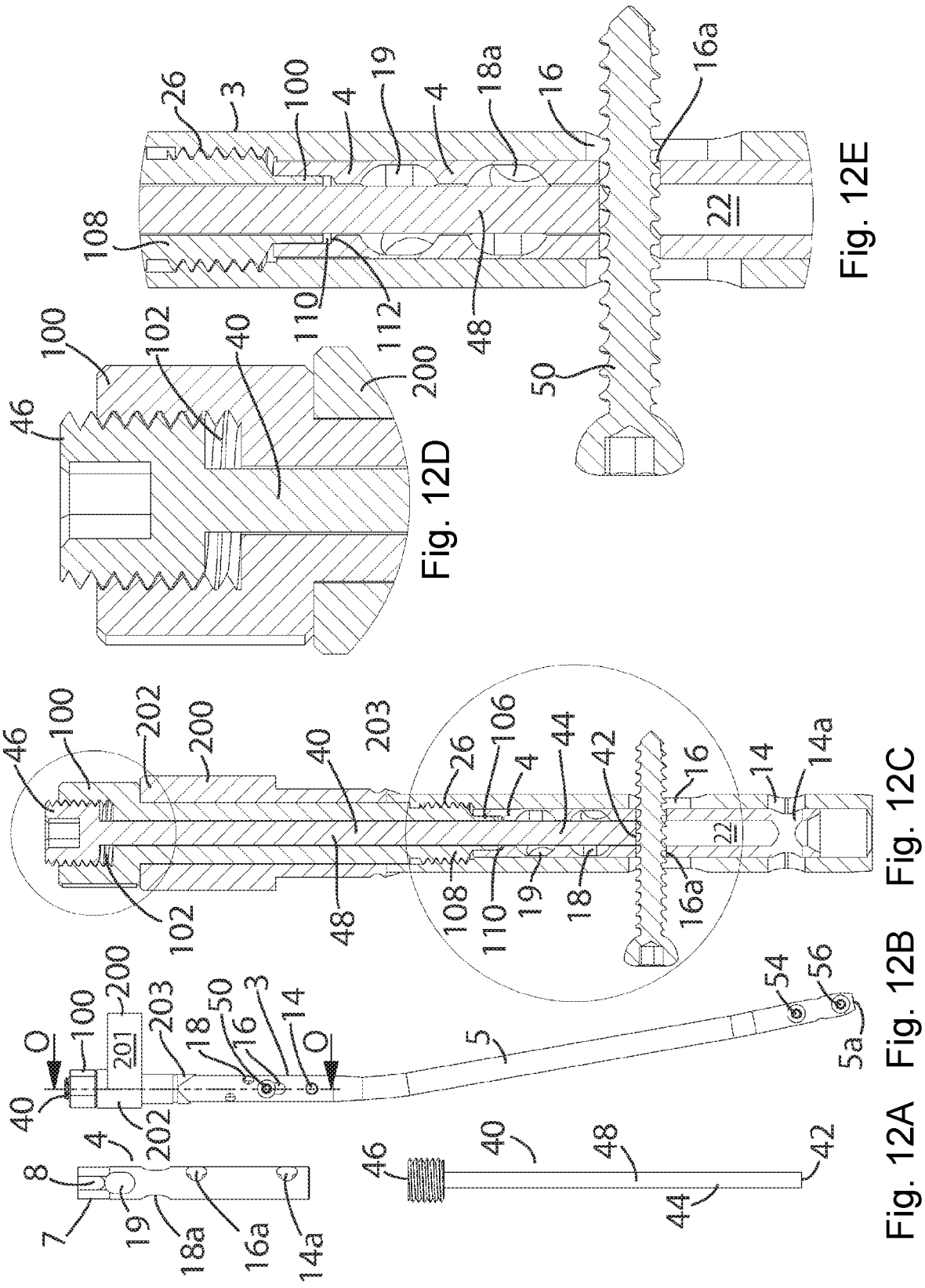

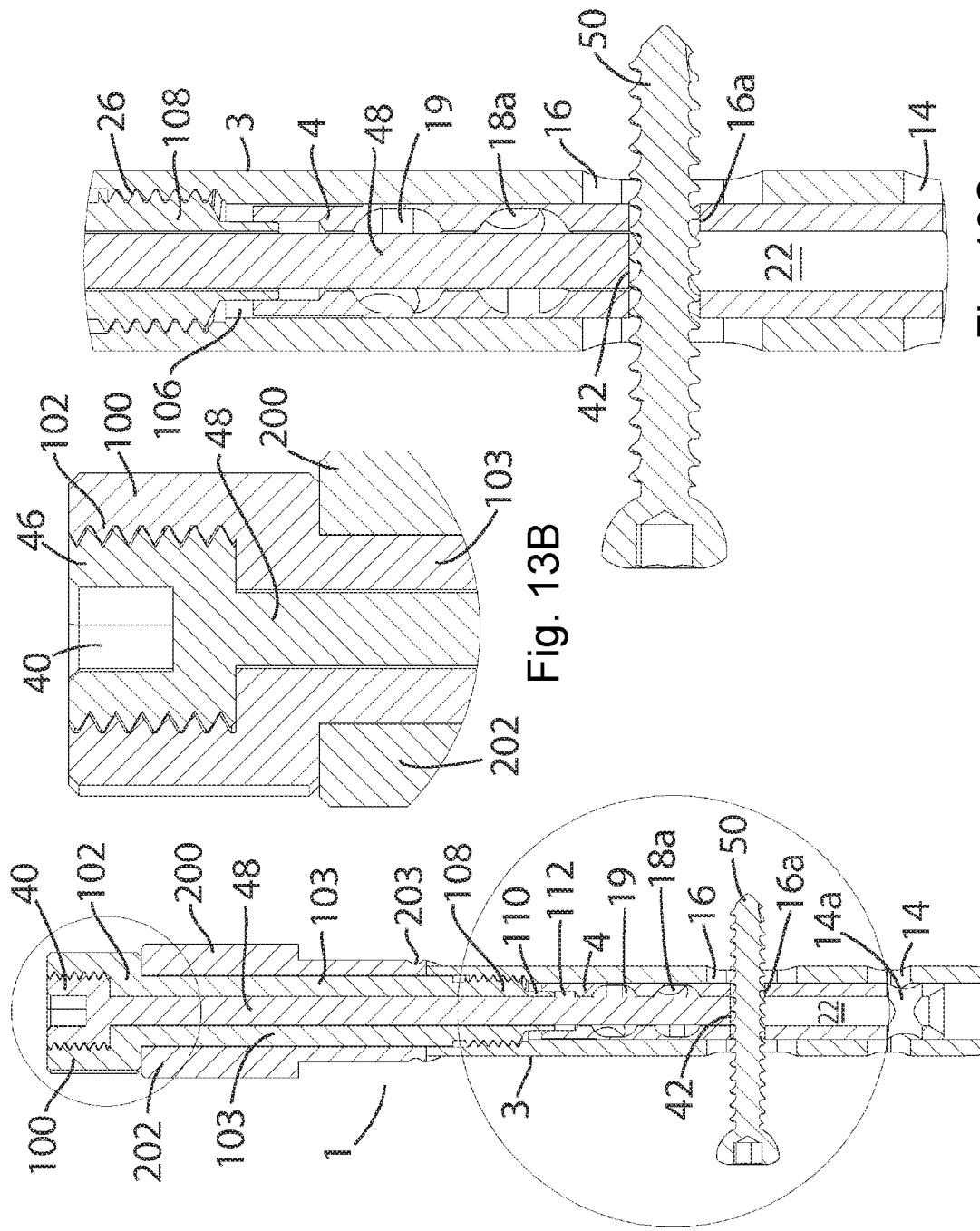

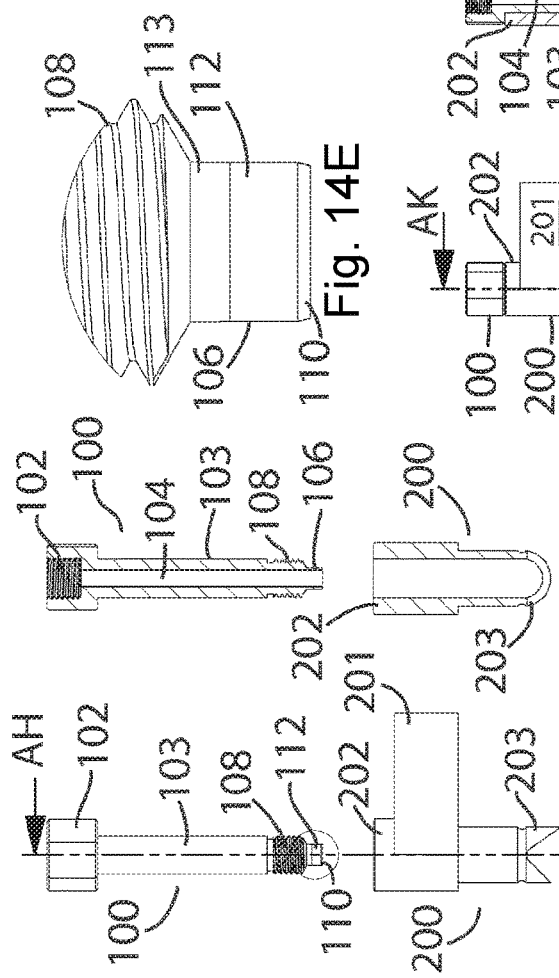
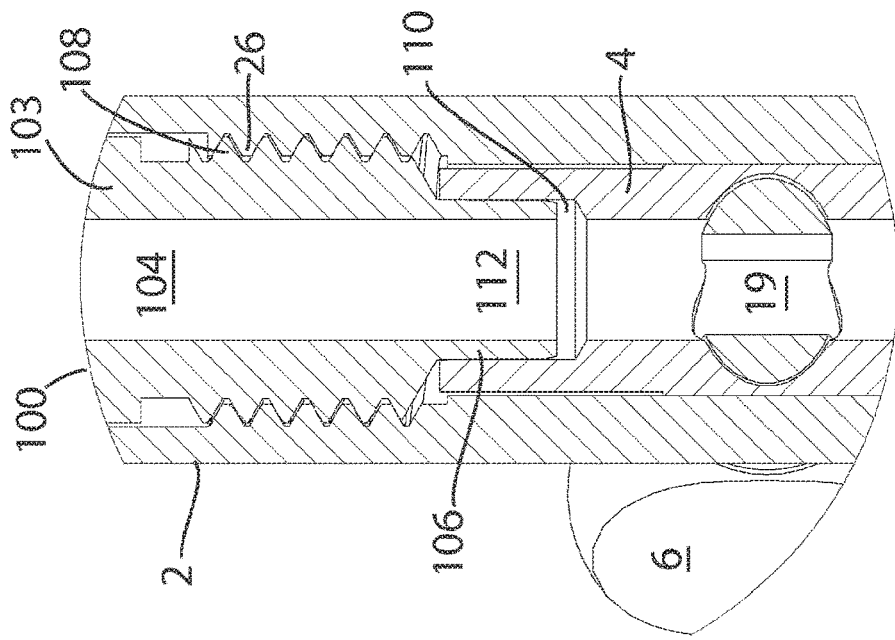
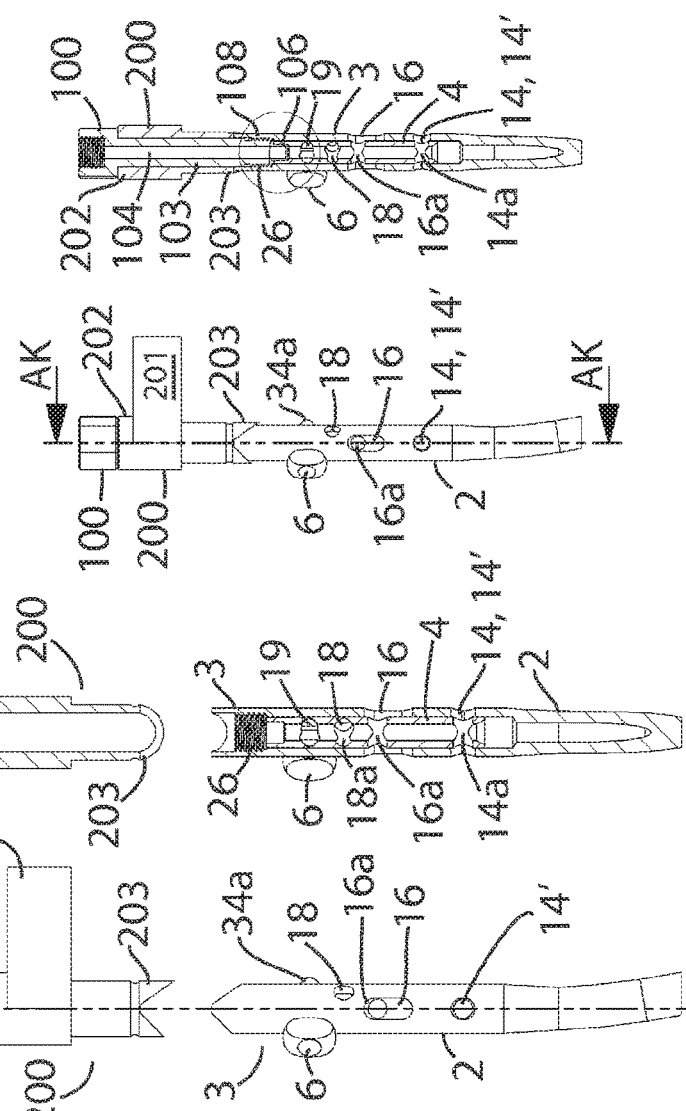

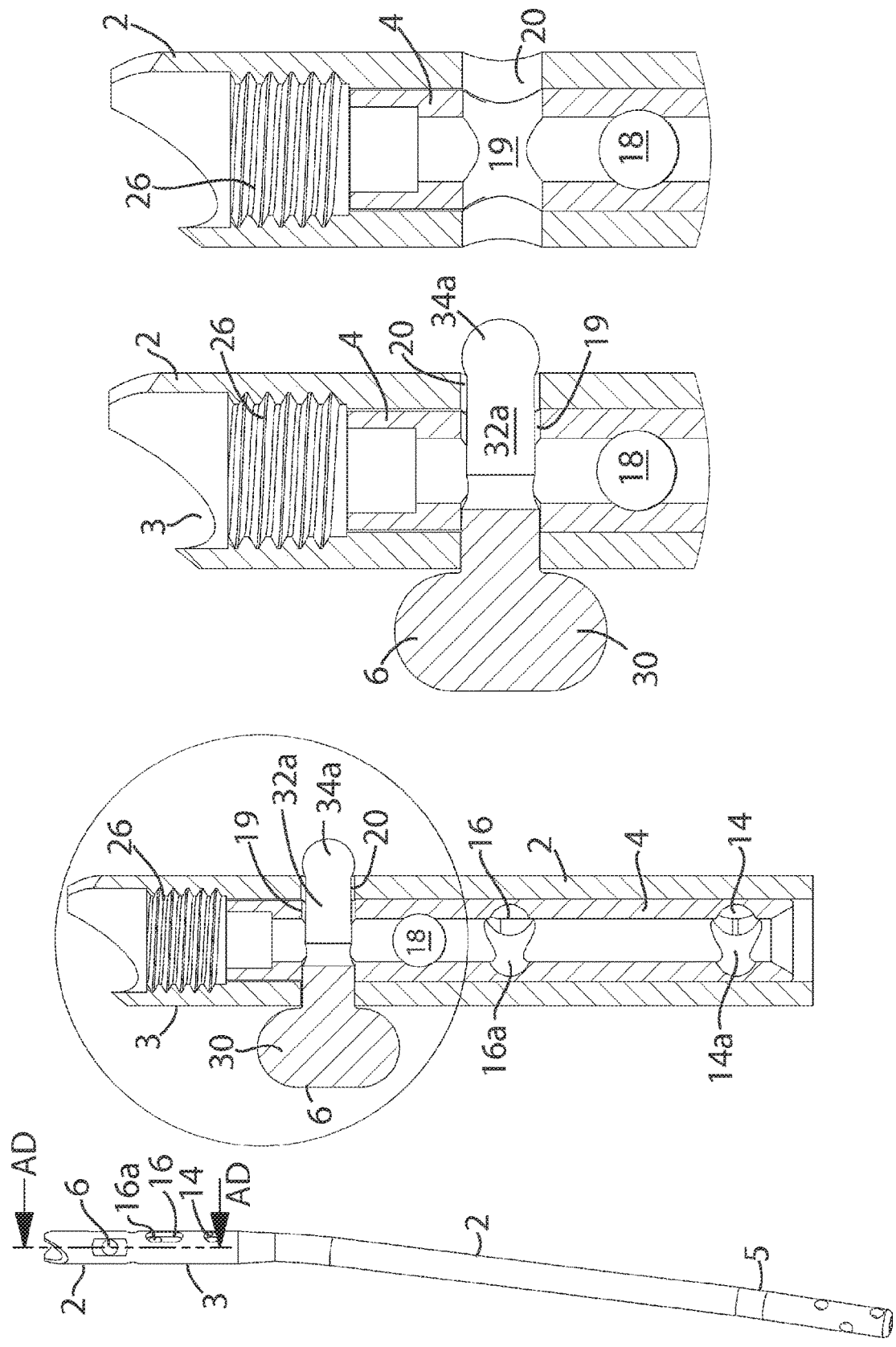

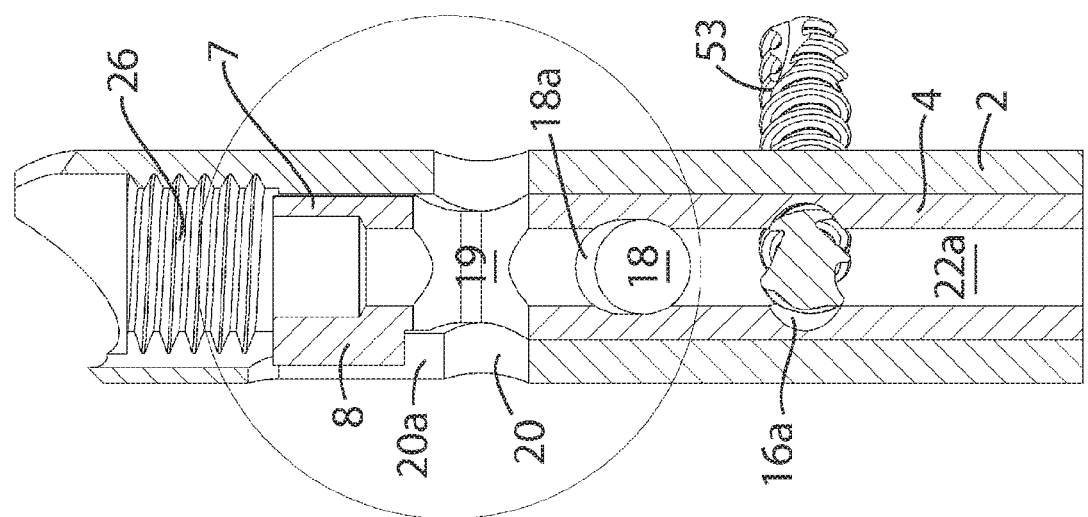
Fig. 16D
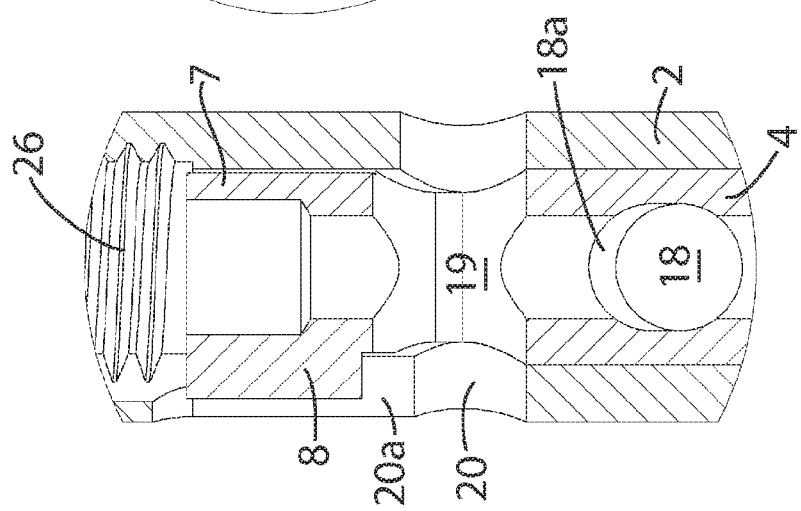
Fig. 16C
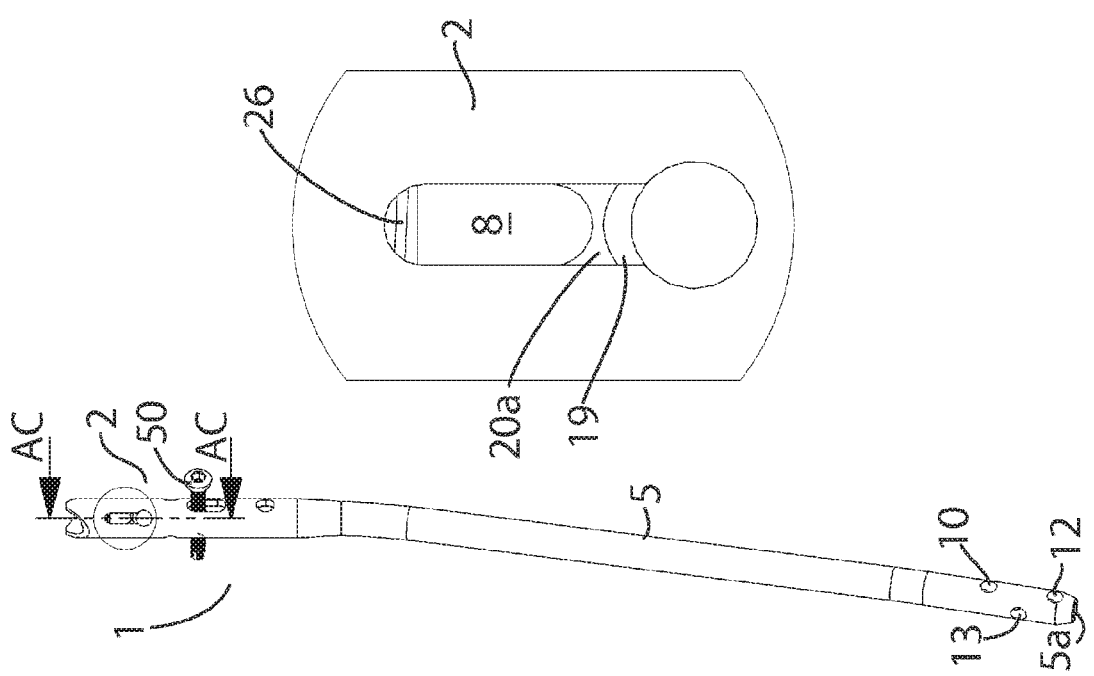
Fig. 16B
Fig. 16A

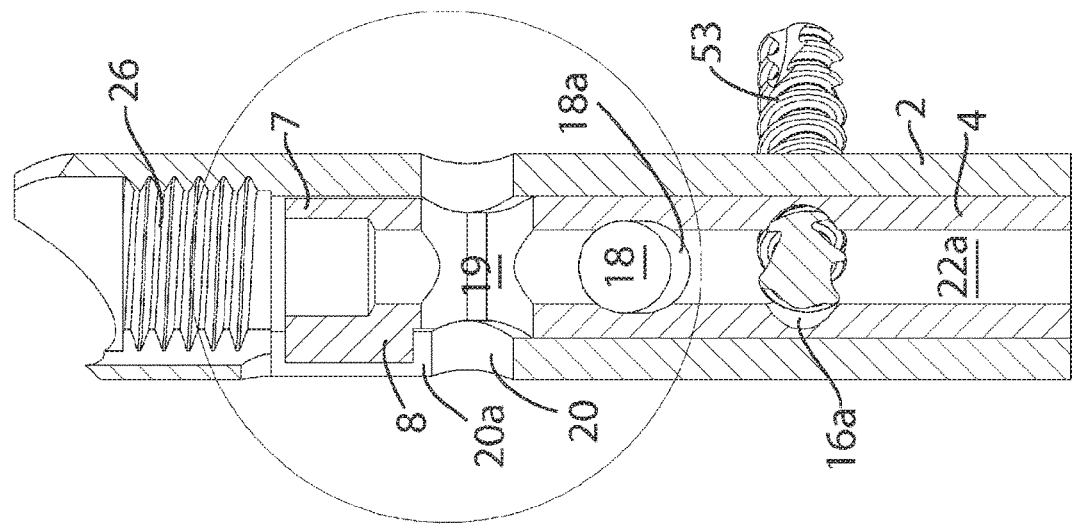
Fig. 17A
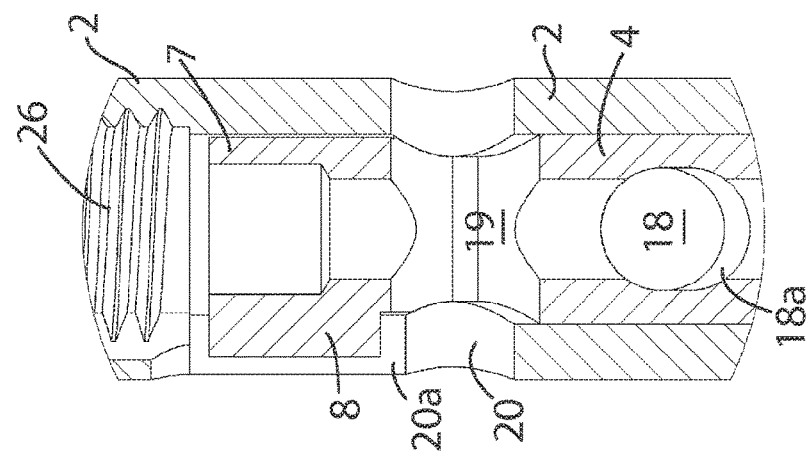
Fig. 17B
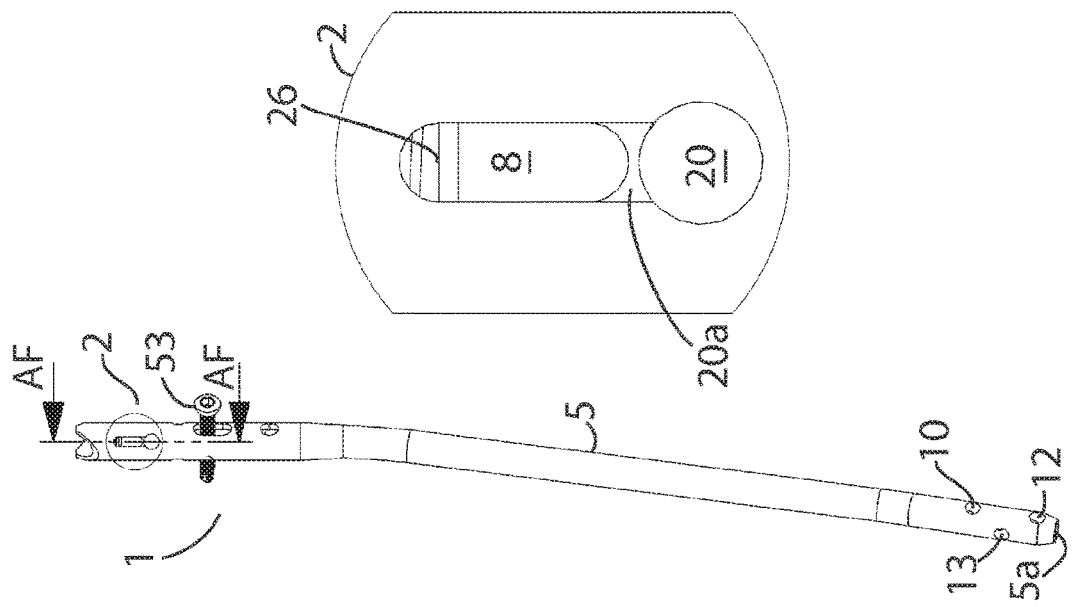
Fig. 17C
Fig. 17D

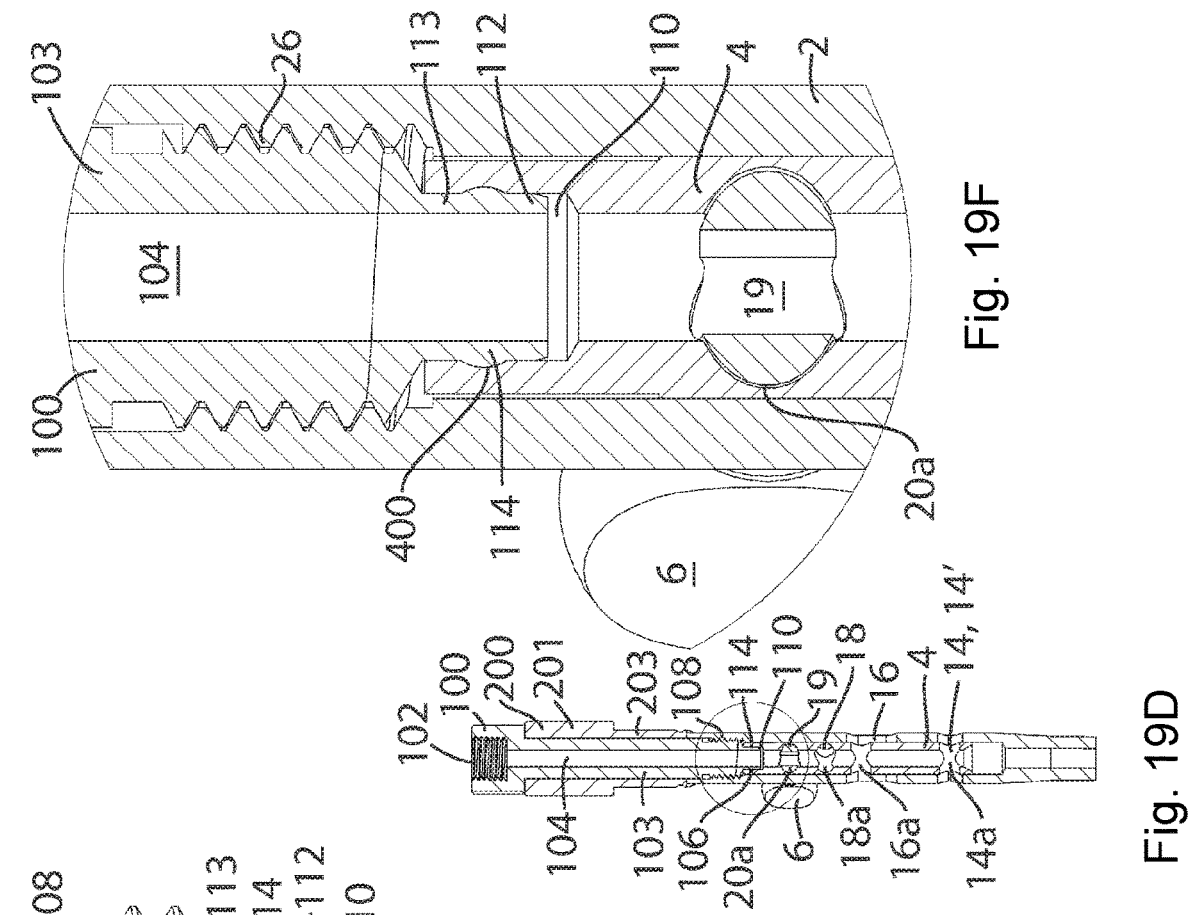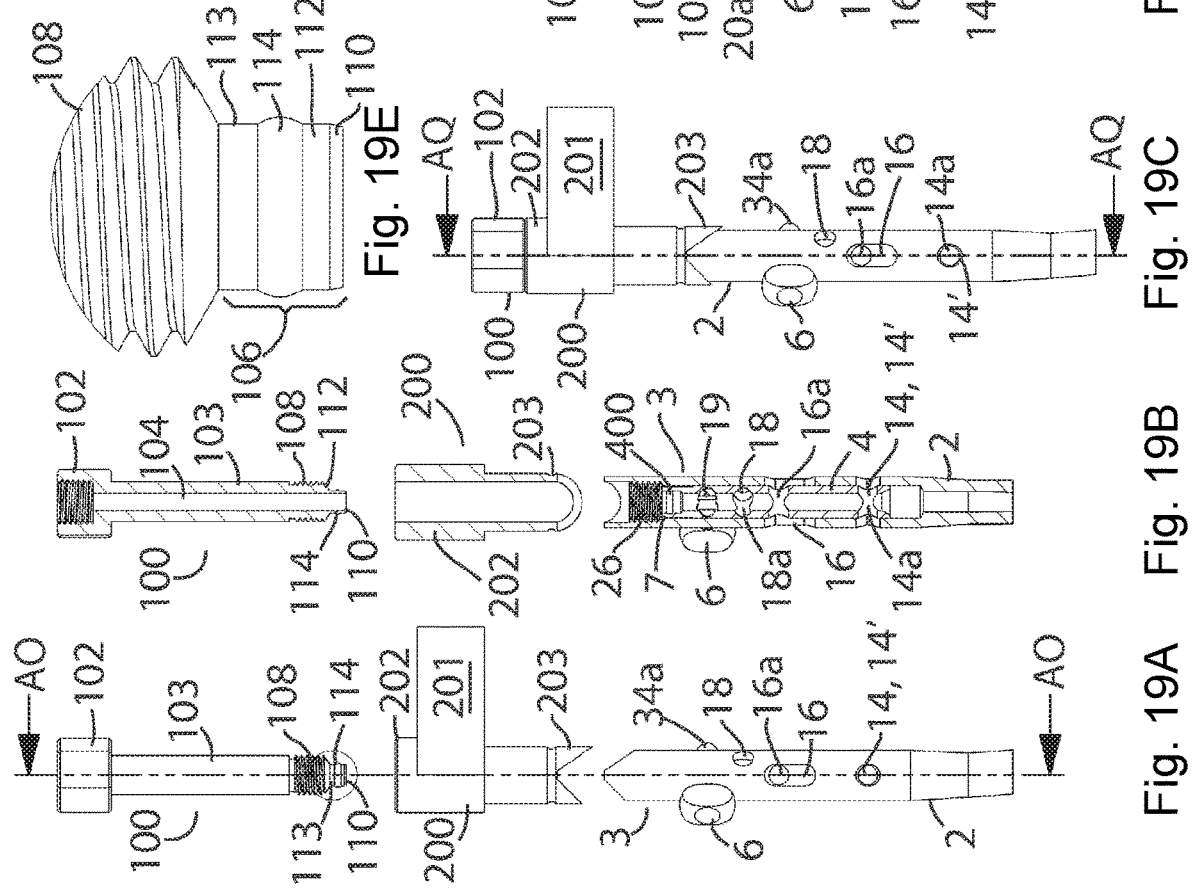

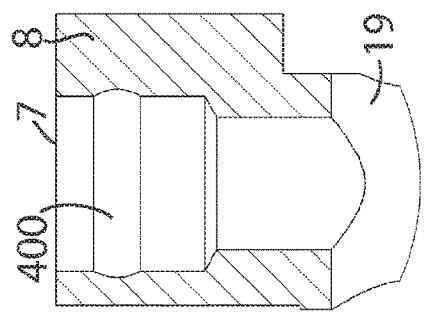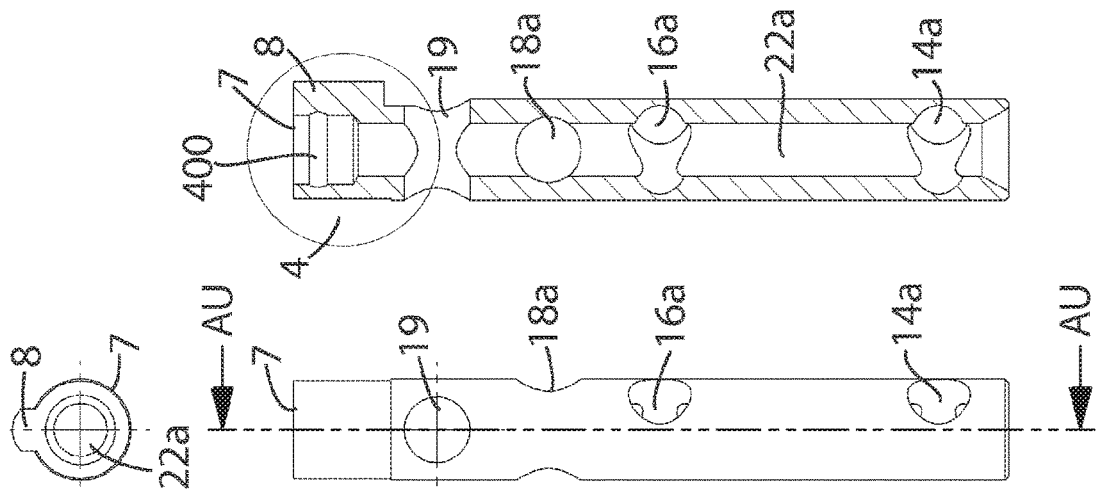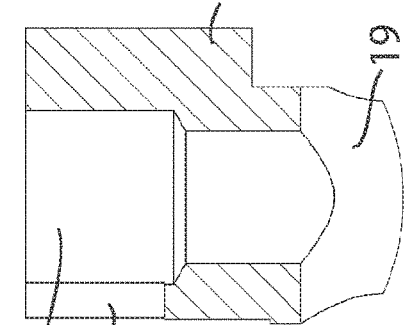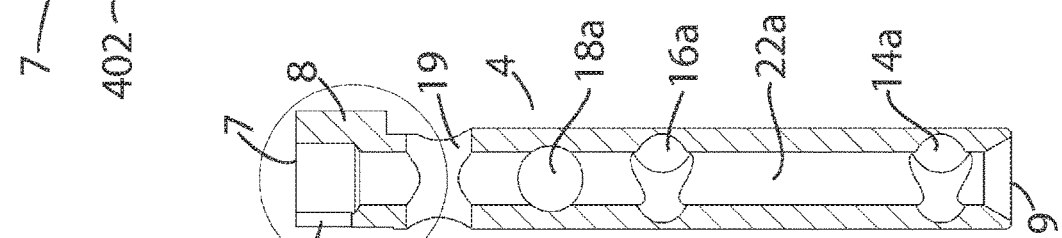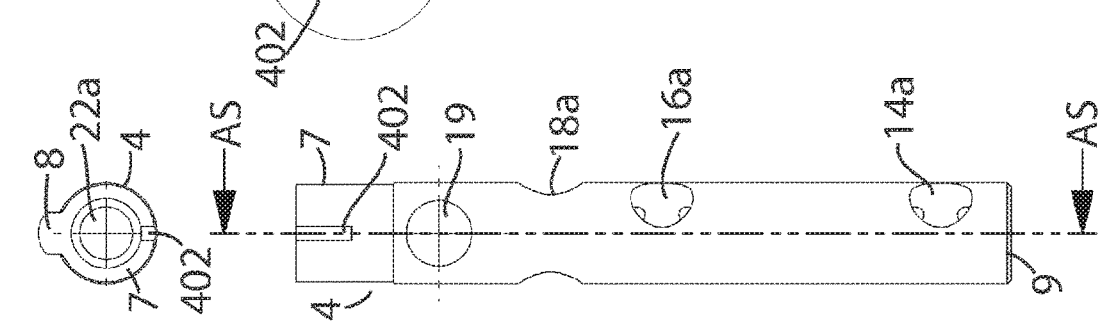
Fig. 20A  Fig. 20B  Fig. 20C  Fig. 20D  Fig. 20E  Fig. 20F

INTRAMEDULLARY NAIL SYSTEM

CROSS-REFERENCE TO RELATED APPLICATIONS

This application is the National Stage of International Application No. PCT/EP2017/058343, filed Apr. 7, 2017, which claims the benefit of Provisional Application No. 62/322,711, filed Apr. 14, 2016, and European Application No. 16165436.3, filed Apr. 14, 2016. The contents of these applications are hereby incorporated by reference in their entirety.

FIELD OF THE INVENTION

The invention relates to an intramedullary nail. In particular, the invention relates to an intramedullary nail system comprising a nail stem and a fastener, and a method for assembling the same.

BACKGROUND TO THE INVENTION

Fractures of the tibia are among the most serious long bone fractures, due to their potential for non-union, mal-union, and long-term dysfunction, as well as their propensity for open injury. Intramedullary nails have been in use for some time as aids in healing bone fractures and are the gold standard treatment option for such fractures. Intramedullary nailing acts as an internal splint and permits early weight bearing along with fracture healing.

WO 2011/018778 describes an intramedullary nail comprising a first part (an insert) having a first opening to receive a first fixture for engagement with a first bone fragment; a second part (a nail stem) having a second opening to receive a second fixture for engagement with a second bone fragment; and a motion assembly (a spring) which allows limited axial relative movement of the inset and nail stem. The insert is constrained to move axially only within the nail stem.

The method disclosed in U.S. patent application Ser. No. 11/627,575 involves an intramedullary implant (a nail) defining a longitudinal bore, and a cannulated movable member (a fastener) receivable within the longitudinal bore and telescopically movable relative to the longitudinal bore. The fastener is a two-piece assembly defined by a plurality of guiding bores for bone fasteners, and is movable between a fastener engagement position and a fastener disengagement position. The fastener moves distally downwards in the elongated slot when force is applied by the locking member. This method principally proposes to loosely align the fastener orientations relative to the stem, but the fastener's non-circular cross-section has significant clearance and means it is not possible to control angular rotation while allowing very small axial movement after the bone screws are inserted.

The problems with intramedullary nails currently being used is that axial interfragmentary motion, which helps to stimulate healing, is largely generated by elastic flexure of the implant during active weight bearing. Patients who are unable, unwilling, or instructed not to engage in weight bearing may not achieve sufficient elastic flexure in an existing implant to enable optimal healing conditions. Furthermore, several nails currently in use have features that are designed to increase the torsional stiffness of the implant because torsional motion at the fracture site disrupts healing. These design features increase construct stiffness by minimizing or eliminating relative movement between the bone screws and the apertures through which they pass. This effectively reduces torsional instability, but also increases axial stiffness, which further reduces the potential for mechanical stimulation of healing in minimally weight bearing patients.

It is an object of the present invention to overcome at least some of the above-mentioned problems.

SUMMARY OF THE INVENTION

According to the present invention there is provided, as set out in the appended claims, an intramedullary nail system (1) comprising a nail stem (2) having a multi-featured proximal end (3), a distal end (5) and a central conduit (22) configured to accommodate a fastener (4) having a proximal end (7), a distal end (9) and a central shaft (22a), wherein the fastener (4) comprises a stop (8) extending laterally from the proximal end (7) relative to a vertical axis of the fastener (4) and which is configured to matingly engage with an internal wall (3a) of the multi-featured proximal end (3) to provide control over rotational and distal movement of the system (1) when secured with a bone screw.

In one embodiment, the internal wall (3a) of the multi-featured proximal end (3) of the nail stem (2) further comprises a longitudinal indentation (11) which provides clearance for the stop (8) when the fastener (4) is placed within the central conduit (22) of the nail stem (2). Preferably, the longitudinal indentation (11) is in communication with a slot (20a) and a hole (20) on the internal wall (3a) of the proximal end (3). More preferably, the stop (8) matingly engages with the slot (20a) to provide variable restraint over rotational and distal movement of the system (1).

In one embodiment, the distal movement of the fastener (4) within the nail stem (2) is limited by the engagement of the stop (8) within the dimensions of the slot (20a) and the dimensions of the hole (20) in the nail stem (2).

In one embodiment, there is provided an intramedullary nail system (1) comprising a nail stem (2) having a multi-featured proximal end (3), a distal end (5) and a central conduit (22) configured to accommodate a fastener (4) having a proximal end (7), a distal end (9) and a central shaft (22a), wherein the fastener (4) comprises a stop (8) extending laterally from the proximal end (7) relative to a vertical axis of the fastener (4) and which is configured to matingly engage with an internal wall (3a) of the multi-featured proximal end (3), the internal wall (3a) further comprising a longitudinal indentation (11) in communication with a slot (20a) and a hole (20) on the internal wall (3a), in which the longitudinal indentation (11) provides clearance for the stop (8) when the fastener (4) is placed within the central conduit (22) and wherein distal movement of the fastener (4) within the nail stem (2) is limited by the engagement of the stop (8) within the dimensions of the slot (20a) and the dimensions of the hole (20) in the nail stem (2) to provide control over rotational and distal movement of the system (1) when secured with a bone screw.

In one embodiment, the nail stem (2) further comprises at least one hole (18, 20), an aperture (14), at least one slot (16, 20a), and at least one micro-slot (14',18') having a smaller longitudinal diameter relative to the longitudinal diameter of the slot (16) configured to accommodate a bone screw. Preferably, the aperture (14) and the slot (16) are parallel and symmetric relative to each other. Preferably, the micro-slot (14') and the slot (16) are parallel and symmetric relative to each other. Preferably, the holes (18,20) and the micro-slot (18') having a smaller longitudinal diameter relative to the longitudinal diameter of the slot (16) are offset relative to the slot (16).

It should be understood that the micro-slots (14',18') have a smaller longitudinal diameter relative to the longitudinal diameter of the slot (16) of the nail stem (2).

In one embodiment, the holes (18, 20), micro-slot (14) having a smaller longitudinal diameter relative to the longitudinal diameter of the slot (16) and the slot (20a) are perpendicular to each other, and are offset from the aperture (14) and the slot (16). Preferably, the holes (18, 20), the micro-slot (14) having a smaller longitudinal diameter relative to the longitudinal diameter of the slot (16) and the slot (20a) are offset at an angle of between 70° and 120° to each other.

In one embodiment, the fastener (4) further comprises at least one hole (14a, 16a, 18a, 19) configured to accommodate a bone screw. Preferably, the hole (14a) has a smaller diameter relative to the longitudinal diameter of the micro-slot (14') of the nail stem (2). Ideally, the holes (14a, 16a) are parallel to each other.

In one embodiment, the holes (18a, 19) are perpendicular to each other and are offset at an angle of between 70° and 120° relative to the holes (14a, 16a).

In one embodiment, the proximal end 7 of the fastener (4) further comprises a slit (402).

In one embodiment, the proximal end 7 of the fastener (4) further comprises a radial indentation (400).

In one embodiment, the system (1) further comprises an alignment pin (6) adapted for securing the fastener (4) within the nail stem (2) during transport and use.

In one embodiment, the alignment pin (6) comprises a grip (30) and a prong (38), the prong (38) having a pair of flexible arms (32a, 32b) descending and conjoined at a base (36). Ideally, the flexible arms (32a, 32b) further comprise bulbous tips (34a, 34b) configured to pass through the holes (14a, 16a, 18, 10, 18a, 19, 20), aperture (14), the slots (16, 20a) and micro-slots (14',18').

In one embodiment, applying a consistent force to the flexible arms (32a, 32b) causes the arms (32a, 32b) to compress and allow the bulbous tips (34a, 34b) to pass through the holes (14a, 16a, 18, 10, 18a, 19, 20), aperture (14), slots (16, 20a), and the micro-slots (14',18').

In one embodiment, the system further comprises an insertion bolt (100) configured to matingly engage with the fastener (4) and/or the alignment pin (6) in the nail stem (2). Preferably, the insertion bolt (100) comprises a threaded proximal end (102), a conduit (104), and a threaded distal end (108) having a flange (106) extending distally therefrom. More preferably, the flange (106) comprises a co-axial section (110), a tapered section (113) and a parallel section (112) extending distally from the distal end (108) and configured to engage with the proximal end (7) of the fastener (4).

In one embodiment, the flange (106) further comprises a berm (114) that is configured to matingly engage with the fastener (4). Ideally, the berm (114) is sandwiched between the parallel sections (112, 113).

In one embodiment, rotational movement of the insertion bolt (100) engages with the proximal end (7) of and presses against the fastener (4).

In one embodiment, the rotational movement of the insertion bolt (100) presses against the fastener (4) which is held by the alignment pin (6) in the axial position.

In one embodiment, when the alignment pin (6) is removed, the fastener (4) is held in position.

In one embodiment, the system (1) further comprises a locking bolt (40) configured to matingly engage with a proximally placed bone screw in the nail stem (2).

In one embodiment, the locking bolt (4) comprises a proximal threaded section (46) and a distal straight rod (48) connected thereto, wherein the rod (48) comprises an interface (42) on its distal end (44), which is configured to interact with a proximal bone screw.

In one embodiment, rotational movement of the locking bolt (40) presses against the proximally placed bone screw and advances the fastener (4) distally to close the bone fracture gap.

In one embodiment, the placement of a bone screw (50, 52, 53, 54, 56) in a hole (18, 20, 14a, 16a, 18a, 19), a slot (16), a micro-slot (14',18') or an aperture (14) secures the fastener (4) and nail stem (2) in place.

In one embodiment, the placement of the bone screws (50, 52) parallel to each other in the hole (14a, 16a), aperture (14) and the slot (16) provides a (micro-dynamisation) locking configuration. Preferably, the (micro-dynamisation) locking configuration is adapted to mediate controlled axial movement over a short distance while preserving torsional stability of the system (1). Preferably, the fastener (4) can move distally and proximally over a distance of 0.01-2 mm. Preferably, the fastener (4) can move distally and proximally generally greater than 1.5 mm but no more than 2 mm.

In one embodiment, the placement of the bone screws perpendicular to each other in the holes (18, 18a, 20, 19) provides a (cross-locking configuration) in which one or more bone screws (50, 52) are placed in an oblique orientation relative to the screws placed parallel to each other in the hole (14a, 16a), aperture (14) and the slot (16). Preferably, the (cross-locking) configuration is adapted for use in unstable proximal fracture patterns.

In one embodiment, the placement of a bone screw (50) in the hole (16a) and the slot (16) provides an alternative (full dynamisation) locking configuration. Preferably, the (full dynamisation) locking configuration is adapted to allow more axial movement than in the (micro-dynamisation) locking configuration where bone screws (50, 52) are placed parallel to each other in the hole (14a, 16a), aperture (14) and the slot (16), while maintaining the construct torsional stability.

In one embodiment, the system (1) further comprises an end cap (58) adapted to matingly engage with a threaded portion (26) of the nail stem (2). Preferably, wherein rotational movement of the endcap (58) advances the fastener (4) distally against one or more proximally placed bone screws and rigidly locking the system (1) to prevent axial and torsional motion.

In one embodiment, the system (1) further comprises at least one hole (10, 12, 13) at a distal end (5a) of the nail stem (2) adapted to accommodate a bone screw (54, 56).

In one embodiment, the nail stem (2) and the fastener (4) have a central conduit (22, 22a) to allow placement over a guidewire.

In one embodiment, the distal end (5) of the nail stem (2) is offset by an angle of between 5° and 25° relative to the vertical axis of the proximal end (3).

In one embodiment, the distal end (5) of the nail stem (2) is aligned on-axis to the vertical axis of the proximal end (3).

In one embodiment, the proximal end (3) of the nail stem (2) is adapted for attachment to one bone fragment and the distal end (5) of the nail stem is adapted to attach to a second bone fragment.

In another embodiment, there is provided, as set out in the appended claims, a kit of parts for use in repairing a bone fracture, the kit comprising an intramedullary nail system (1) as described above.

In one embodiment, the kit further comprises an alignment pin (6).

In one embodiment, the kit further comprises a locking bolt (40) and an insertion bolt (100).

In one embodiment, the kit further comprises a locking end cap.

In one embodiment, the kit further comprises a non-locking end cap.

One aspect of the invention is an intramedullary nail system as described herein for use in a method for repairing a bone fracture, the method comprising the steps of:
Positioning the affected limb of the patient;
Opening a portal to the medullary canal at the proximal tibia by separating the soft tissue and drilling a short entry passage;
Reaming the medullary canal if deemed appropriate by the surgeon;
Selecting the appropriate nail diameter and length from radiographic templating and taking reference to the last reamer size;
Attaching the surgical instruments to the nail with the fastener and alignment pin in place, such that the fastener becomes constrained from motion relative to the nail by the insertion bolt;
Removing the alignment pin;
Inserting the nail into the medullary canal;
Confirming fracture alignment by radiographic means;
Drilling for and inserting distal bone screws of number and alignment chosen according to the surgeon's judgement using a free-hand technique;
Carrying out the compression locking procedure if desired, otherwise
Drilling for and inserting proximal bone screws of number and alignment chosen according to the surgeon's judgement and using the provided targeting instrumentation to achieve:
  Micro-dynamisation locking mode,
  Full-dynamisation locking mode,
  Cross-locked mode, or
  Compression-locked mode;
Removing the surgical instruments from the IM system;
Inserting an endcap according to the surgeon's judgement, either:
  Standard endcap, or
  Locking endcap to achieve a substantially rigid locking configuration; and
Closing all soft tissue.

In one embodiment, the material of construction is suitably a durable, rigid and biocompatible material, for example, implant-grade titanium alloys (such as titanium-aluminium-vanadium (Ti-6AL-4V ELI64) or titanium-aluminium-niobium (Ti-6Al-7Nb)), stainless steel (316L or 316LVM), or any other metal alloy, composite, polymer material or combination thereof that is suitable for load-bearing application as an in vivo implant.

The advantages of the intramedullary nail described herein is that rotational control is provided by the circular outer surfaces of the fastener and inner diameter of nail stem, combined with the stop on the fastener mating with the slot in nail stem. The clearance for the fastener placement is an off-centre semicircle (incorporating a narrow longitudinal indentation) that is machined from the proximal end of the nail to interface with the slot on the nail proximal stem. The fastener can advance distally by 1-2 mm for compression locking during implantation; and can advance distally by 0.01-2 mm for micro-dynamisation locking by using the slot in the stem; and can advance distally by 5-7 mm for full dynamisation locking by using the slot with aligned hole in the nail proximal stem. Placing the features in this way reduces the amount of material removed as the hole becomes effectively an extension of the slot. If a longer slot were employed this would be a stress raiser and also make the overall length of the IM nail system too long. Having a hollow internal shaft throughout the nail stem and fastener allows placement of the nail over a guidewire. A threaded section on the internal wall of the proximal end of the nail stem allows placement of instrumentation during implantation and various endcaps after nail placement.

In the specification, the term "micro-dynamisation locking" should be understood to mean securing the IM nail system as described herein in position using bone screws and wherein positioning the bone screws in medio lateral openings (long dynamisation slot and aperture distal to long slot) of the nail stem and the corresponding fastener holes allows controlled axial low force movement of the proximal bone fragment with limited rotation while the IM nail system is secured in situ. In this configuration, the fastener can slide distally and proximally over approximately 0.01-2 mm, preferably 0.1-2 mm, more preferably 0.5-1.5 mm, ideally 0.75-1 mm, or greater than 1.5 mm but no more than 2 mm, and generally greater than 0.5 mm but no more than 1.5 mm, with this distance determined by the dimensions of the micro-dynamisation slot in the stem and of the bone screw that is placed in the aligned hole in the fastener.

In the specification, the term "cross-locking configuration" should be understood to mean locking of the IM nail system described herein in position using bone screws, and where the positioning of the bone screws in the holes of the proximal end of the nail stem, and the fastener, is chosen such that at least two screws are oriented in different planes. When viewed along the axis of the nail stem, the central axes of the cross-locked screws cross to form an "X"-type shape. This provides a semi rigid locking of the system dependant on the degree of dimensional variation between the bone screw and relevant hole.

In the specification, the term "full dynamisation locking" should be understood to mean locking of the IM nail system described herein in position using bone screws, and where the positioning of a bone screw in the long slot of multi-featured proximal end of the nail stem and the fastener allows controlled axial movement of the proximal bone fragment over a range of approximately 5-7 mm, or as much as is desired, while the IM nail system is secured in situ. The dynamisation distance determined by the dimensions of the dynamisation slot in the stem and of the bone screw that is placed in the aligned hole in the fastener.

In the specification, the term "a substantially rigid locking configuration" should be understood to mean a configuration of the IM nail system described herein, in which the nail is locked in position relative to the bone fragments using bone screws and endcaps, where the positioning of the bone screws in the multi-featured proximal end of the nail stem and the fastener is restricted by the endcap to allow very little or no relative movement of any component. In this configuration, significant movement of the bone fragments can only occur due to elastic flexure of the IM nail system components during active weight bearing applied by the patient.

In the specification, the term "compression locking procedure" should be understood to mean an intraoperative action taken by the surgeon to compress the fracture gap by engaging the compression bolt with the dynamisation screw only, prior to insertion of other bone screw(s). This action serves to bring the ends of the proximal and distal bone fragments into closer proximity prior to definitive fixation by the insertion of one or more additional proximal bone screws. During compression locking, the fastener can advance distally by a distance less than or equal to the length of the full dynamization slot in the nail stem minus the diameter of the bone screw, or a smaller distance that may be chosen by introducing one or more internal physical features within the nail stem or nail insertion and locking instrumentation (e.g. insertion handle) to limit the axial movement of the fastener, the compression bolt, or both.

In the specification, the term "compression bolt" should be understood to mean a reusable surgical instrument temporarily placed within the cannulus of the nail and instrumentation guides that exerts an axial translational force on the bone screw placed in the dynamisation slot and serves to push the fastener and the proximal bone fragment in the distal direction, thereby bringing the bone fragments into closer proximity.

In the specification, the term "multi-featured proximal end" should be understood to mean the proximal end of the nail stem having a suite of features. The suite of features consists of holes, apertures, longitudinal indentation or slots configured to accommodate bone screws, an alignment pin or fastener. The longitudinal indentation along the internal wall of the proximal end first provides clearance for a stop on the fastener to engage with a slot on the nail stem, and a further interfacing hole allows the stop to advance distally when the fastener is placed within the central conduit of the nail stem.

In the specification, the term "unstable proximal fracture patterns" should be understood to mean bone fractures occurring near the knee joint that may be considered clinically suitable for fixation by IM nailing, but are not mechanically stable due to the orientation of the fracture line(s).

In the specification, the term "non-locking endcap" or "standard endcap" should be understood to mean an endcap which sits in the threads at the proximal end of the nail stem and does not engage with any other component. The endcap's only purpose is to prevent bone ingrowth into the nail and sometimes to extend the nail length proximally by 5-15 mm, as is common practice in intramedullary nailing.

In the specification, the term "locking endcap" should be understood to mean an endcap which sits in the proximal threads of the nail stem and has the same function as the non-locking endcap, except that is also engages with the fastener. The locking endcap provides a distally-directed force by means of the screw threads to compress any bone screw(s) carried by the fastener firmly into the distal face of each corresponding hole in the nail stem. This produces a substantially-rigid construct.

In the specification, the term "berm" should be understood to mean a raised barrier separating two areas.

It should be understood that the specification provides description of the order of the holes and slots from the proximal to the distal ends of the nail stem and fastener. However, these slots and holes could be re-arranged in a different order to form a different embodiment with exactly the same functionality (see, for example, FIGS. 7A-C and FIGS. 8A-E).

BRIEF DESCRIPTION OF THE DRAWINGS

The invention will be more clearly understood from the following description of an embodiment thereof, given by way of example only, with reference to the accompanying drawings, in which:

FIG. 1A illustrates an exploded view and FIG. 1B illustrates a side view, of an IM nail system of the present invention.

FIG. 2A illustrates a side view of the nail stem, FIG. 2B illustrates a sectioned view of a proximal end of the nail stem along axis A-A, and FIG. 2C illustrates a sectional top view of the nail stem along axis B-B.

FIG. 6A illustrates the interface between the nail stem and the fastener, while

FIGS. 7A-D illustrate a micro-dynamisation locking configuration.

FIGS. 11A-D illustrate a configuration to obtain a substantially rigid locking configuration after the bone screws are placed in the IM nail system, by inserting a locking endcap.

FIG. 12A illustrates the fastener and a locking bolt prior to insertion in the IM nail system as described above and combined, as illustrated in FIG. 12B, in a compression locking mode having the locking bolt and an insertion bolt in place to provide closure of the fracture gap after the nail is in place. FIG. 12B also illustrates an instrument guidance apparatus in place, affixed the top of the IM nail system. FIG. 12C is an illustration of section O-O from FIG. 12B. FIG. 12D is closer detail P from FIG. 12C, and FIG. 12E is a closer detail Q, also from FIG. 12C. In the FIG. 12C and FIG. 12D, it is clear that the locking bolt has not been advanced to achieve full engagement with the physical stop in the nail stem and maximal closure of the gap between the bone fragments.

FIGS. 13A-C illustrates the compression locking mode with the locking bolt fully engaged with the insertion bolt and bone screw.

FIG. 14A illustrates an exploded view of the insertion bolt, the instrumentation apparatus and the IM nail system with the alignment pin in place; FIG. 14B is a cross-section of FIG. 14A; FIG. 14C is a side view of the nail stem, instrumentation apparatus, insertion bolt and pin together as a single unit, while FIG. 14D is a cross-section of FIG. 14C; FIG. 14E is a closer view of detail AJ showing the distal tip features of the insertion bolt of FIG. 14A, and FIG. 14F is a view of detail AL showing the insertion bolt engaged with the fastener of FIG. 14D.

FIG. 15B illustrates a cross-section of the IM nail system with the with the alignment pin in place as depicted in FIG. 15A; FIG. 15C is a closer view of detail AE of FIG. 15B, and FIG. 15D is a view of detail AF without the alignment pin.

FIGS. 16A-D illustrates the initial position of the fastener in the IM nail system during the compression locking procedure.

FIGS. 17A-D illustrates the adjusted position of the fastener in the IM nail system during the compression locking procedure.

FIG. 19A illustrates an exploded view of the insertion bolt, the instrumentation apparatus and the IM nail system with the alignment pin in place; FIG. 19B is a cross-section of FIG. 19A; FIG. 19C is a side view of the nail stem, instrumentation apparatus, insertion bolt and alignment pin together as a single unit, while FIG. 19D is a cross-section of FIG. 19C; FIG. 19E is a closer view of detail AJ showing the distal tip features of the insertion bolt of FIG. 19A, and FIG. 19F is a view of detail AL showing the insertion bolt engaged with the fastener of FIG. 19D.

FIG. 20A illustrates a side view of the fastener of the invention, while FIG. 20B illustrates a cross-section of FIG. 20A along axis AS-AS. FIG. 20C is a closer view of detail AC. FIG. 20D illustrates a side view of an alternative embodiment of the fastener of the invention, while FIG. 20E illustrates a cross-section of FIG. 20D along axis AU-AU. FIG. 20F is a closer view of detail AT.

DETAILED DESCRIPTION OF THE DRAWINGS

Like all intramedullary nails, the intramedullary nail system described herein sits within the hollow space inside the bone. Screws placed above and below the fracture stabilise the bone fragments to allow healing. Small axial movements along the length of the bone help speed up healing, while twisting movements slow down healing. The nail described herein offers both controlled axial motion and very little twisting, providing the optimum healing conditions at the fracture site, reducing both the healing time and time to patient weight bearing.

In addition to controlled axial micro-motion and torsional stability, the nail system described herein offers proximal and distal interlocking options similar to current products. The nail described herein has a proximal end and a distal end similar to others nails of the prior art. In addition, the nail proximal stem has an internal circular surface adapted to accept a fastener. A further interface between the nail and fastener manifests itself as a slot (longitudinal indentation) that extends axially along the nail stem in communication with a hole (shaped like a keyhole) to mate with a stop on the proximal end of the fastener. The balance of these interfaces provides tuneable, relative movement in both axial and torsional directions.

Figures 1A, 1B:
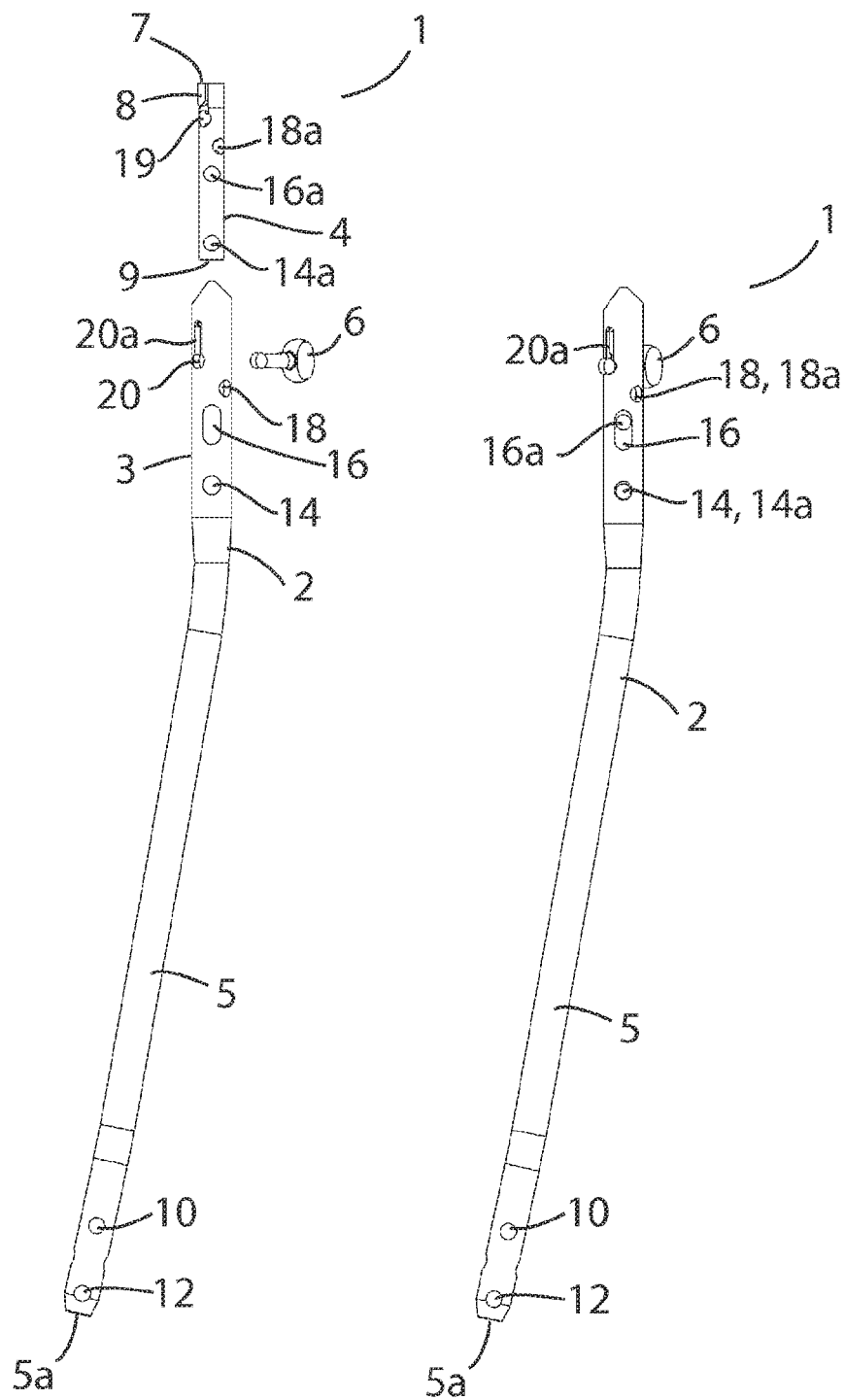
FIGS. 1A and 1B illustrate a general embodiment of an intramedullary (IM) nail system of the present invention.

Referring now to the figures, where FIG. 1A illustrates a general embodiment of an intramedullary (IM) nail system of the present invention. Specifically, FIG. 1A illustrates an exploded view of an IM nail system of the present invention, and is generally referred to by reference numeral 1. The IM nail system 1 illustrated here comprises a nail stem 2, a fastener 4 and an alignment pin 6. FIG. 1B illustrates a side view of the IM nail system 1 with the fastener 4 and alignment pin 6 in situ.

Figure 8D:
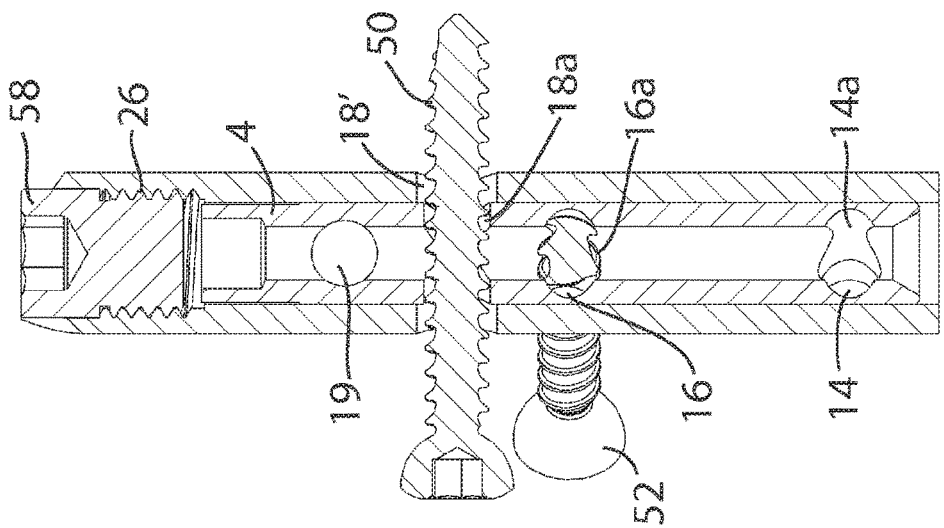
FIGS. 8A-D illustrate an alternative micro-dynamisation locking configuration.

The nail stem 2 comprises a distal end 5 and a multi-featured proximal end 3. The nail stem 2 is made from a single piece of material. The distal end 5 may be approximately 5° to 25° off the proximal axis of the nail stem 2 or may be aligned on-axis. The distal end 5 comprises holes 10, 12, 13 which are each configured to accommodate a bone screw. The multi-featured proximal end 3 of the nail stem 2 comprises an aperture 14, which lies distal and parallel to slot 16 with the same line of symmetry. The aperture 14 can be either in the form of a slot (an elongated aperture 14') or a hole (a substantially circular aperture 14). The holes or slots found in either the nail stem 2 or the fastener 4 of the system 1 are defined by the internal dimensions of a cut-out section (hole or elongated slot) in the nail stem 2 and the fastener 4, respectively. The internal dimensions are generally defined by a circumference edge. The multi-featured proximal end 3 further comprises medial lateral holes 18 and 20 positioned oblique to and above slot 16. The holes 18, 20 are also oblique to each other. The hole 20 also encompasses a slot 20a in fluid communication with the proximal edge of the hole 20, forming a keyhole-type opening. All of the holes 10, 12, 18 and 20, aperture 14, as well as the slot 16 and the slot 20a, are configured to accommodate a bone screw. A micro-slot 14',18' (see FIGS. 11 and 8, respectively) are also configured to accommodate a bone screw.

The fastener 4 also comprises a proximal end 7 and a distal end 9. The proximal end 7 of the fastener 4 comprises a stop 8 that extends laterally from the proximal end 7 relative to the vertical axis of the fastener 4, and which is adapted to mate with the slot 20a and hole 20 of the nail stem 2. Just below the stop 8 is a hole 19, which aligns with the hole 20 on the nail stem 2 when the stop 8 is engaged with the slot 20a. The fastener 4 also comprises holes 18a, 16a and 14a, which are aligned to match the hole 18, slot 16 and aperture 14, respectively, on the nail stem 2. The hole 14a of the fastener 4 is generally of a smaller diameter than the width/diameter of the aperture 14 of the nail stem 2, which forms a micro-slot 14' (see FIG. 11). FIG. 1B illustrates the alignment of the fastener 4 with the nail stem 2 with the alignment pin 6 secured in holes 19, 20 of the fastener 4 and nail stem 2, respectively. In this position, holes 14a, 16a and 18a are in line with aperture 14 (micro-slot 14'), slot 16 and hole 18 (or micro-slot 18'), respectively.

FIG. 2A illustrates a side view of the nail stem 2, while FIG. 2B illustrates a sectioned view of the multi-featured proximal end 3 of the nail stem 2 along axis A-A. The nail stem 2 has a hollow central conduit 22 that narrows to a bore 24. The bore 24 extends to the tip 5a of the distal end 5 of the nail stem 2. The multi-featured proximal end 3 of the nail stem 2 also comprises a threaded section 26. FIG. 2C illustrates a sectional top view of the nail stem 2 along axis B-B. The multi-featured proximal end 3 of the nail stem 2 has an internal wall 3a that defines the conduit 22. The internal wall 3a further comprises a longitudinal indentation 11 that accommodates the stop 8 of the fastener 4. The presence of the longitudinal indentation 11, and the shape of the opening of the multi-featured proximal end 3 of the nail stem 2, ensures that there can only be one orientation that the fastener 4 can be placed within the nail stem 2.

Figures 3A, 3B:
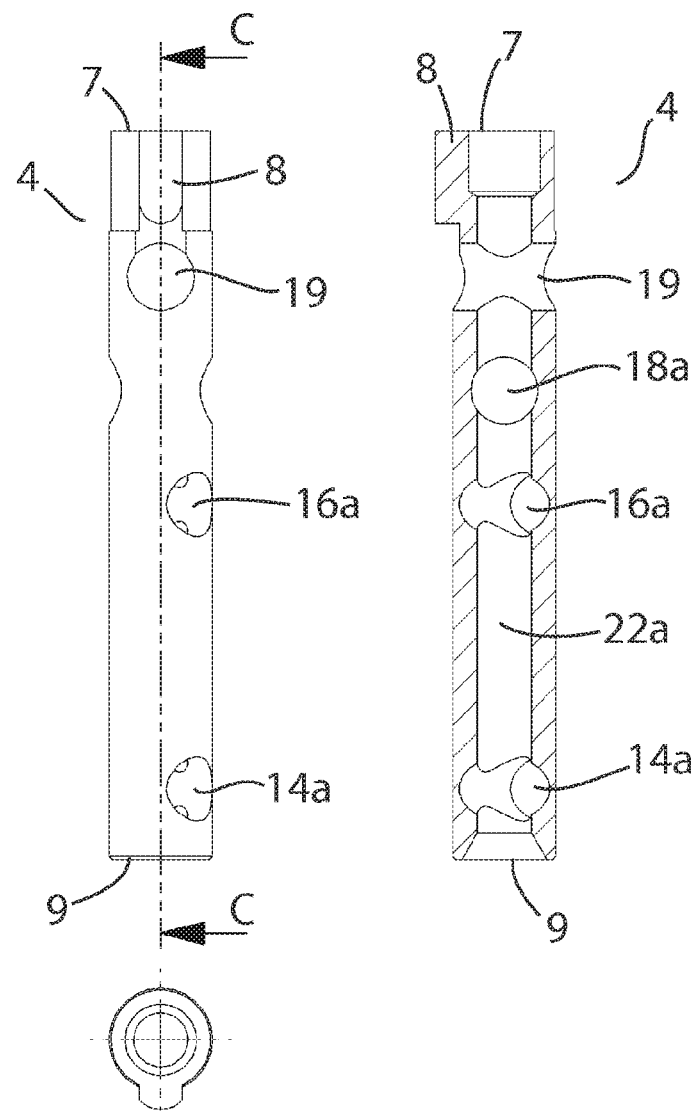
FIG. 3A illustrates a side view of the fastener. The section along axis C-C of the fastener is illustrated in FIG. 3B.

FIG. 3A illustrates a side view of the fastener 4, with the stop 8 facing forward. The section along axis C-C of the fastener 4 (as illustrated in FIG. 3B) shows the stop 8 facing to the left. The fastener 4 is further defined by a hollow central shaft 22a.

As illustrated in FIG. 2B, which is a view of section A-A from FIG. 2A, it can be seen that aperture 14 and slot 16 of the nail stem 2 are parallel to each other and positioned about the same symmetry plane. The holes 18 and 20 (including slot 20a) of the nail stem 2 are perpendicular to each other, and are offset at an angle of, for example, between 30° and 60° from the aperture 14 and the slot 16.

FIG. 3B, which is a view of section C-C from FIG. 3A, it can be seen that holes 14a and 16a of the fastener 4 are parallel and symmetric to each other. The holes 19 and 18a of the fastener 4 are perpendicular to each other are offset at an angle of between, for example, 30° and 60° from the holes 14a and 16a.

Figures 4A, 4B:
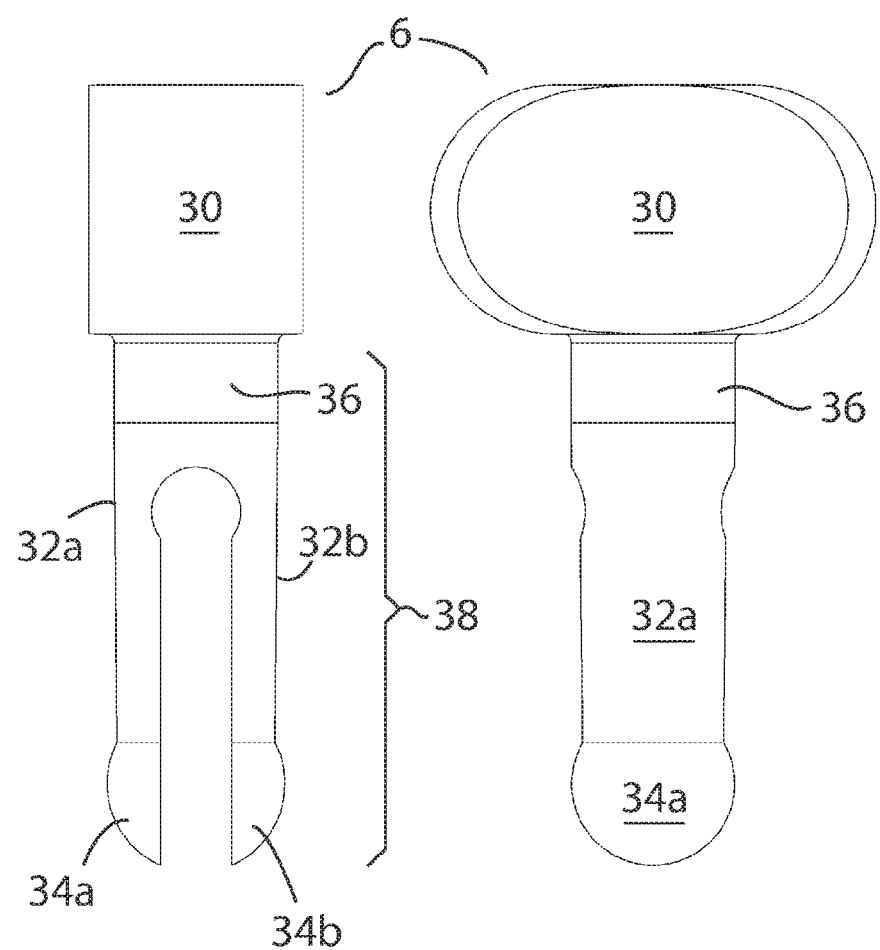
FIG. 4A and FIG. 4B illustrate an alignment pin of the present invention.

FIG. 4A and FIG. 4B illustrate the alignment pin 6. The alignment pin 6 comprises a grip 30 and a prong 38. The prong 38 having a pair of flexible arms 32a, 32b descending and conjoined at a base 36 but taper in so that the width of arms 32a, 32b is narrower than that of the base 36. The flexible arms 32a, 32b are substantially equidistant apart, that is, they are essentially parallel to each other. The flexible arms 32a, 32b each end with a bulbous tip 34a, 34b, respectively, whose width is greater than that of the base 36.

The flexible arms 32a, 32b, the tip 34a, 34b and tapered surface accommodate ease of engagement during placement into any one of the holes found in the nail stem 2 (18 or 20) or fastener 4 (18a, 19). The flexible arms 32a, 32b and the tip 34a, 34b retains the alignment pin 6 in place during transportation, removal from its packaging and during assembly. Inserting the alignment pin 6 maintains the axial position of the fastener 4 in the nail stem 2, through radial location in any one of the holes of the nail stem 2 and fastener 4. This is achieved through the interface of alignment pin base 36 relative to nail stem hole 18/20 or fastener hole 18a/19. The alignment pin 6 allows for a consistent removal force where the flexible arms 32a, 32b compress, allowing the bulbous tip 34a, 34b pass through the holes, 18, 10, 18a, 19, respectively.

Figure 5A:
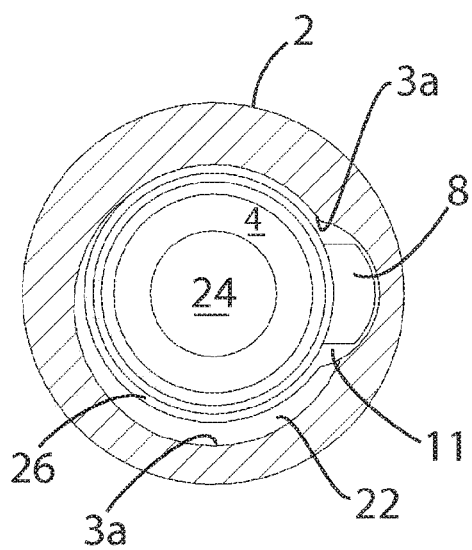
FIG. 5A and FIG. 5B illustrate sectional views of FIG. 5C along axes D-D and E-E, respectively.
Figure 5B:
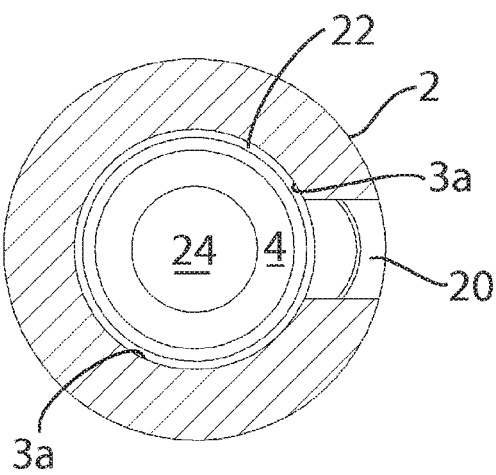
Figure 5C:
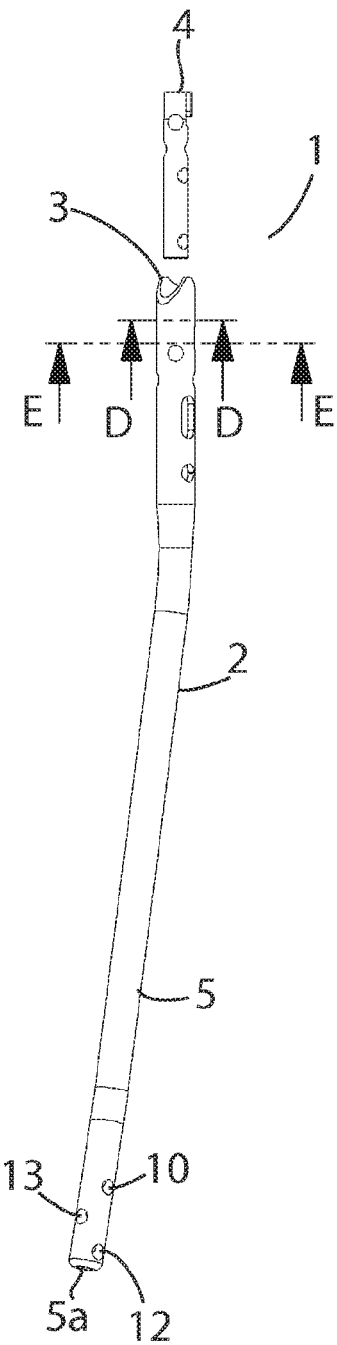

Turning now to FIG. 5A and FIG. 5B, there is illustrated a sectional view of FIG. 5C along axes D-D and E-E, respectively. The fastener 4 can be seen to be configured to fit within the hollow conduit 22 of the nail stem 2, and the stop 8 is configured to pass through the clearance provided by longitudinal indentation 11 and engage the confines of the dimensions of the slot 20a of the nail stem 2. The clearance for the fastener 4 in the conduit 22 of the nail stem 2 is off-centre relative to the central axis of the central shaft 22 (longitudinal indentation 11). The off-centre alignment allows ample room for the mating interaction between the confines of the dimensions of the slot 20a and the stop 8 to occur.

Figure 6A:
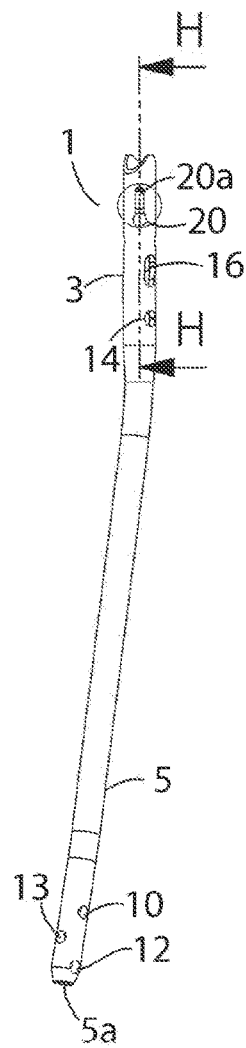
Figure 6B:
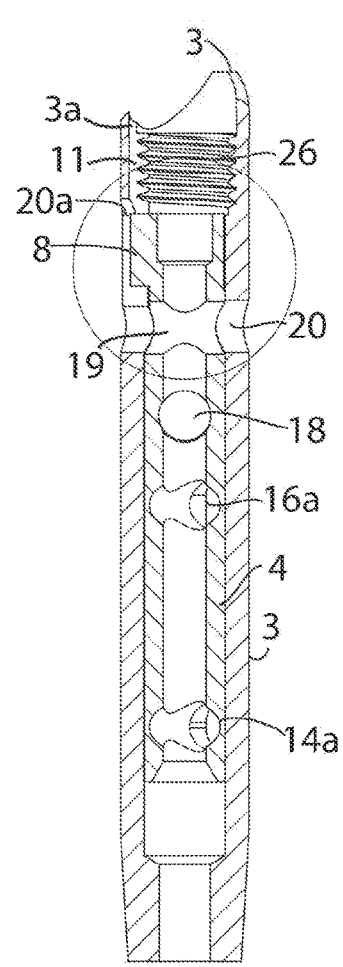
FIG. 6B illustrates a view along axis H-H from FIG. 6A.
Figure 6C:
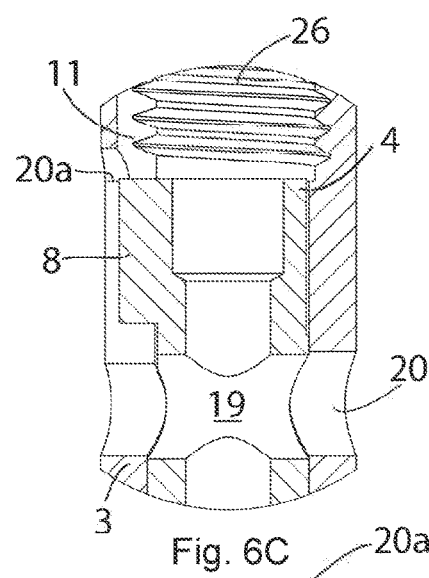
FIG. 6C illustrates a more detailed view (detail J) of the stop of the fastener coming to rest on the surface of the nail stem.
Figure 6D:
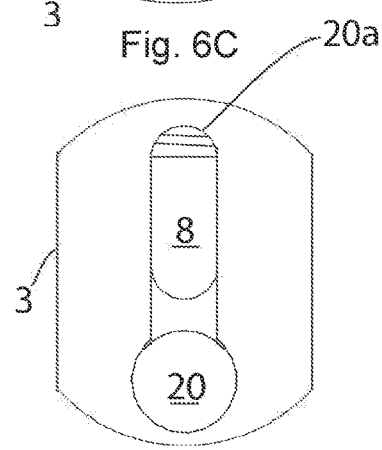
FIG. 6D illustrates a closer view of detail G, which shows the stop mating with the slot of the nail stem.

The interface between the nail stem 2 and the fastener 4 is illustrated, for example, in FIG. 6B where the view along axis H-H from FIG. 6A is given in more detail. The fastener 4 is observed sitting inside the conduit 22 of the nail stem 2. The stop 8 is in the clearance at the distal end of the longitudinal indentation 11, which extends axially along the internal wall 3a of the stem 2. The longitudinal indentation 11 is in communication with the slot 20a and hole 20, which forms a keyhole-type arrangement in the nail stem 2. The stop 8 cannot move beyond the internal dimensions of the hole 20, as the stop 8 comes to rest on a surface 20b of the hole 20. FIG. 6C (and FIG. 15, section PP) shows a more detailed view (detail J) of the stop 8 coming to rest on the surface 20b. FIG. 6D illustrates a closer view of detail G, which shows the stop 8 within the slot 20/hole 20a.

There are a number of different locking configurations that a user may utilise, depending on the locking effect required. Examples of said locking configurations are outlined below.

The first option is a micro-dynamisation locking configuration. This is illustrated in FIG. 7A, FIG. 7B and FIG. 7C (detail K from FIG. 7A) where a controlled micro-dynamisation locking mode is shown. In this locking mode, at least two bone screws 50, 52 are placed in the two medio-lateral holes of the nail stem 2, namely the aperture 14 and the slot 16. In this instance, the longitudinal diameter of the aperture 14 is longer than that of the hole 14a and is termed a micro-slot 14'. The micro-slot 14' (an elongated aperture 14) is lined up with the hole 14a of the fastener 4, while the slot 16 is lined up with the hole 16a of the fastener 4. In this locking configuration, the fastener 4 becomes active. The configuration guides allowed movement (micro-motion) when a small axial force is applied, such as during routine patient activity; the micro-motion distance is defined by the diameter difference of the bone screw 50, 52 relative to the micro-slot 14' (an elongated aperture 14) and slot 16, respectively; and torsional movement is tuned by the fit of the interfaces between the nail stem 2 and the fastener 4. The tolerance between the stop 8 and slot 20a, in combination with the diameter of the fastener 4 and nail stem conduit 22, allow tuneable control of the rotational stability of the fastener 4 relative to the nail stem 2 during axial translational motion. The distal bone screws 54, 56 are also shown in situ in the holes 10, 12, respectively, of the distal end 5 of the nail stem 2.

Figure 8C:
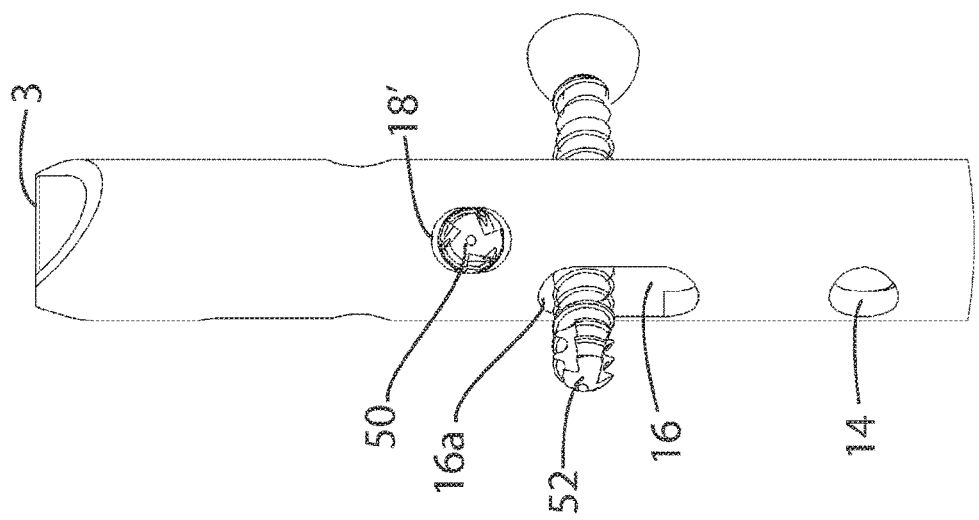
Figures 8A, 8B:
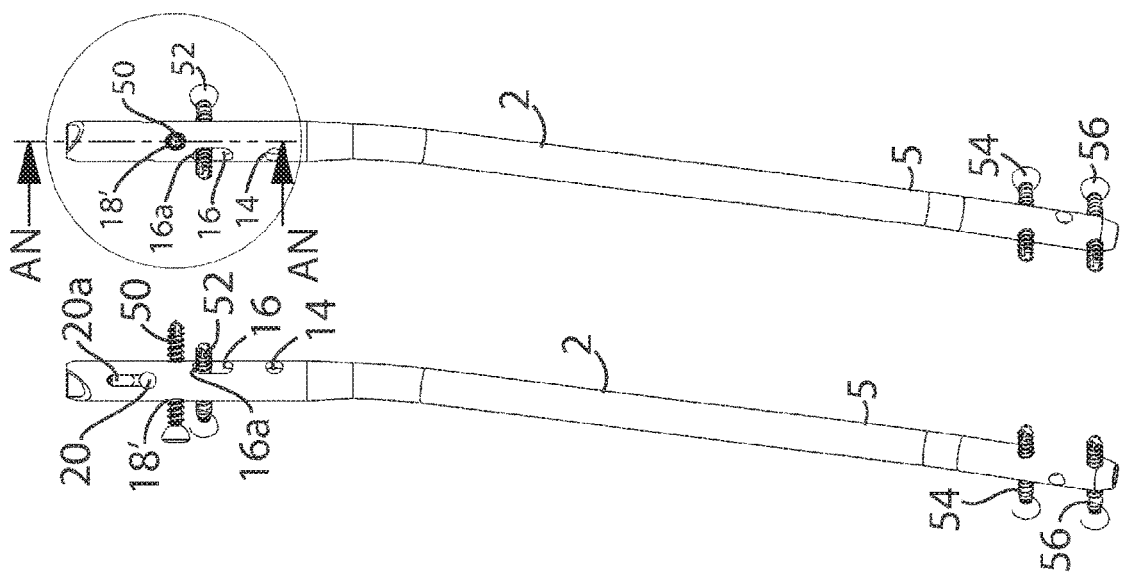

An alternative embodiment of the micro-dynamisation locking mode is illustrated in FIG. 8A, FIG. 8B and FIG. 8C (detail AG from FIG. 8B) where a controlled micro-dynamisation locking mode is shown. In this locking mode, at least two bone screws 50, 52 are placed in two holes of the nail stem 2, namely a micro-slot 18' and the slot 16. The micro-slot 18' is lined up with the hole 18a of the fastener 4, while the slot 16 is lined up with the hole 16a of the fastener 4. The micro-slot 18' has a diameter that is larger than that of the hole 18a of the fastener 4; so as to allow the micro dynamisation movement using a different locking screw position when compared to the configuration of FIG. 7. In the locking configuration presented in FIG. 8, just as in FIG. 7, the fastener 4 becomes active. The configuration guides allowed movement (micro-motion) when a small axial force is applied, such as during routine patient activity; the micro-motion distance is defined by the diameter difference of the bone screw 50, 52 relative to the micro-slot 18' and slot 16, respectively; and torsional movement is tuned by the fit of the interfaces between the nail stem 2 and the fastener 4. The tolerance between the stop 8 and slot 20a, in combination with the diameter of the fastener 4 and nail stem conduit 22, allow tuneable control of the rotational stability of the fastener 4 relative to the nail stem 2 during axial translational motion. The distal bone screws 54, 56 are also shown in situ in the holes 10, 12, respectively, of the distal end 5 of the nail stem 2. This is just one example of where altering the positioning of the slots and apertures from those depicted in the drawings, can lead to the same functional effect.

Figure 9A:
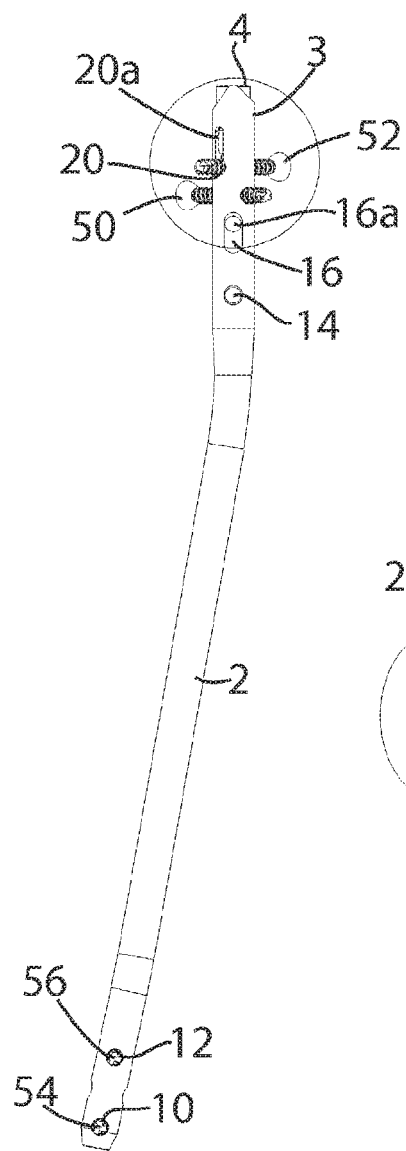
FIG. 9A and FIG. 9B illustrate a cross-locking configuration.
Figure 9B:
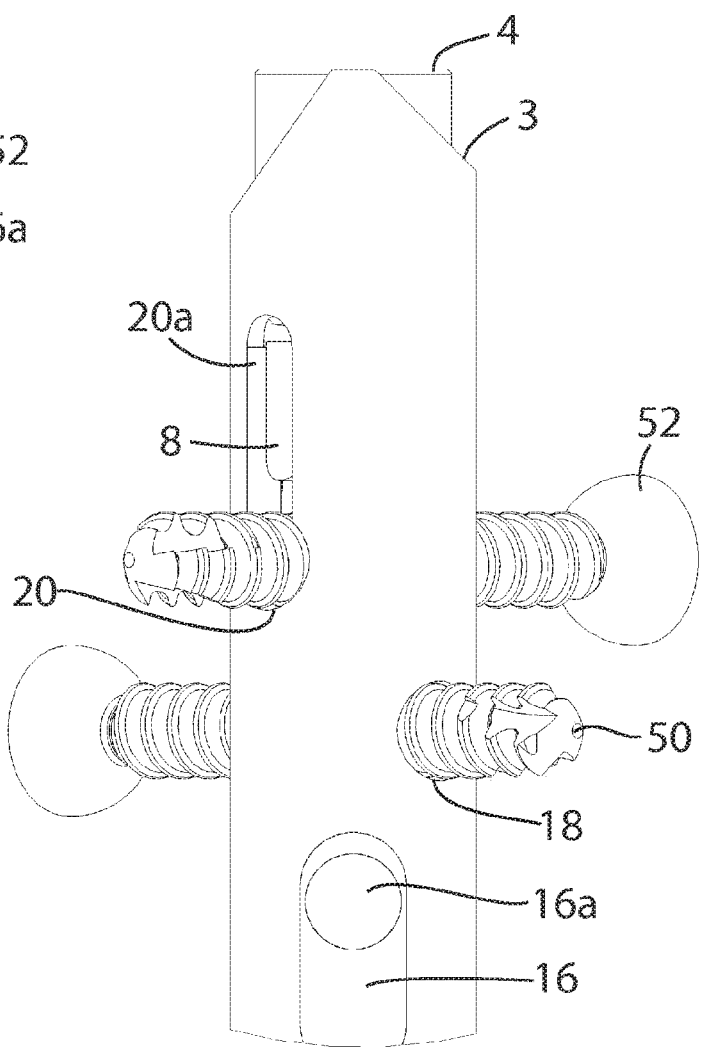

FIG. 9A and FIG. 9B illustrate a cross-locking configuration where the bone screws 50, 52 are placed in the two oblique holes 18, 20, which pair up with holes 18a and 19, respectively, of the fastener 4. In this instance, the fastener 4 has no function per se and merely sits dormant (unmoving) within the longitudinal indentation 11 and slot 20a in the nail stem 2.

Figure 10A:
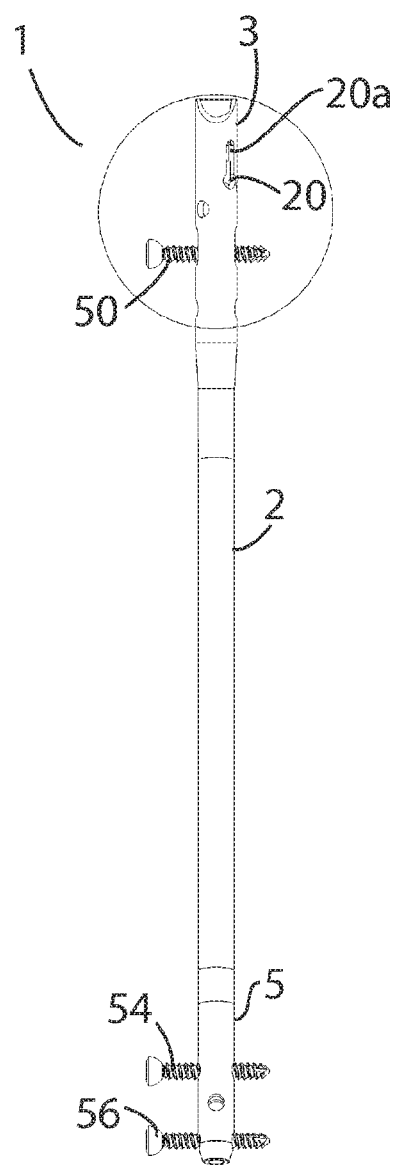
FIG. 10A and FIG. 10B illustrate full dynamisation locking.
Figure 10B:
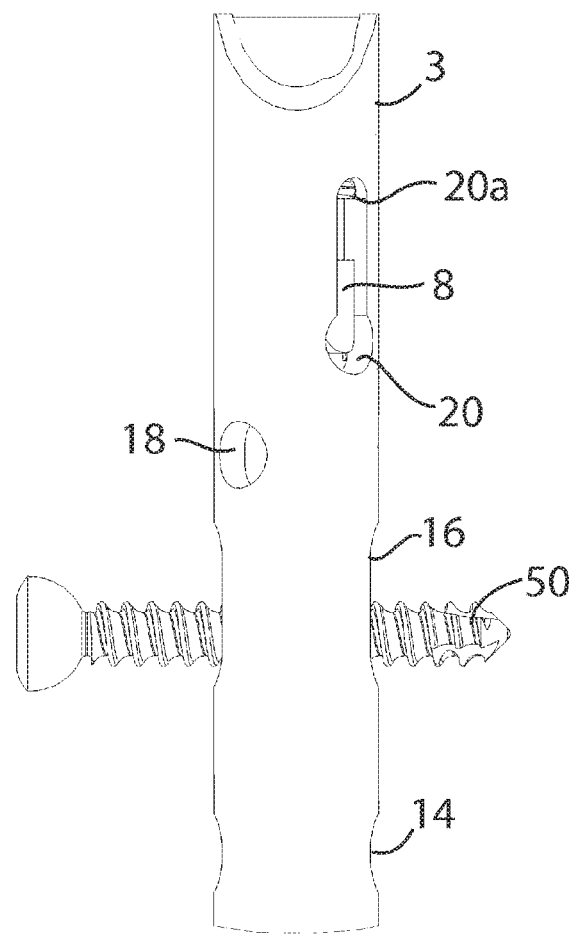

FIG. 10A and FIG. 10B illustrate full dynamisation locking where one bone screw 50 is placed in the slot 16 of the nail stem 2 and the hole 16a of the fastener 4. In this instance, the fastener 4 is also active as it is configured to move up and down the length of the slot 16. The function of this locking configuration is to retain the torsional stability by the interface of the stop 8 and slot 20*a*, while the axial movement is controlled by the interface of the bone screw 50 and the slot 16 on the nail stem 2.

Any other combination of 3 or more bone screws will lock the fastener 4 such that the fastener 4 has no function and merely sits dormant (unmoving) in the nail stem 2.

FIGS. 11A-D illustrate a configuration to obtain a substantially rigid locking configuration after the bone screws have been placed in the IM nail system 1. At least one bone screw 52 is placed in either of the holes 18, 20 in nail stem 2 and 18*a*,19 in fastener 4, and any combination of other bone screws such as bone screw 50 as illustrated, followed by insertion of a locking endcap 58. The locking endcap 58 engages the threaded section 26 of the nail stem 2 and simultaneously presses into the fastener 4, thereby clamping the bone screw 52 rigidly. The endcap 58 advances the fastener 4 distally and, by extension, pushes the bone screw 52 distally against the hole 20 on the nail stem 2. Additional contributions to the rigidity of the IM nail system 1 in situ come from the interfaces of the fastener 4 and nail stem 2 as detailed earlier.

FIG. 12A and FIG. 12B illustrate the IM nail system 1 in a compression locking mode, with FIG. 12C being the view O-O from FIG. 12B. In this mode, bone screws 54, 56 are placed first in the distal end 5*a* of the nail stem 2. A bone screw 50 is then placed in distal slot 16 of the nail stem 2 and hole 16*a* of the fastener 4. Thereafter, the surgeon can control the fracture gap of the broken bone through a locking bolt 40. The locking bolt 40, as illustrated in FIG. 12A, generally comprises a proximal threaded section 46 and a distal straight rod 48 connected thereto. The rod 48 comprises an interface 42 on its distal end 44, which is configured to interact with a previously placed proximal bone screw 50.

The IM nail system 1 includes a compression locking system (see FIGS. 12 and 13) that is in essence a mixture of an instrument guidance apparatus 200, an insertion bolt 100 and a locking bolt 40. The IM nail system 1 is affixed with the instrument guidance apparatus 200 via insertion bolt 100 (see FIG. 14A-F). The instrument guidance apparatus 200 is affixed in the anterior posterior direction to the proximal end 3 of the nail stem 2. The guidance apparatus 200 generally comprises a flange 201, configured to engage further instrumentation to aid in the guided drilling of pilot holes prior to placing bone screws in any proximal hole of the intramedullary nail system 1, and a distal end 203 adapted to matingly engage with the proximal end 3 of the nail stem 2 in one orientation. The insertion bolt 100 generally comprises a threaded proximal end 102, a shaft 103, a central conduit 104, a threaded distal end 108 adapted to engage with the threaded portion 26 of the proximal end of the nail stem 2, and a flange 106 that simultaneously engages with the proximal end of the fastener 4 (see FIGS. 14D and 14F). The detail of the flange 106 is given in FIG. 14E. The flange 106 comprises a co-axial section 110 (relative to shaft 103), a parallel section 112 and a tapered section 113 which is configured to initially engage with the proximal end 7 of the fastener 4. The central conduit 104 is configured to accommodate the distal straight rod 48 of the locking bolt 40 and guidewire passage. Further advancement via the threading of the insertion bolt 100 into the nail stem 2 will engage the tapered section 113 of insertion bolt 100 in the proximal end 7 of the fastener 4 to ensure a rigid interference connection between the fastener 4 and the insertion bolt 100. At this point the alignment pin 6 can be withdrawn and the fastener 4 will be held in place relative to the nail stem 2, with no allowed relative movement.

During the surgical procedure, after the nail stem 2 has been placed inside the medullary canal of the affected bone, the distal straight rod 48 of the locking bolt 40 is placed within the central conduit 104 of the insertion bolt 100 and threaded into the threaded proximal end 102 of the insertion bolt 100 (see FIG. 12C). The locking bolt 40 advances into the conduit 22 of the nail stem 2 and then the central shaft 22*a* of the fastener 4, until it interfaces against the bone screw 50 and is flush with the proximal end 102 of the insertion bolt 100 (see FIGS. 13A and 13C). Further rotation of the locking bolt 40 allows for precise fracture setting/compression, as this will axially move the bone screw 50 relative to the slot 16. After the location is finalised, further bone screws 52, 50 may be placed in the holes 18, 20 to fully secure the IM nail system 1 in place.

During storage, transportation and intra-operative attachment of the insertion handle to the proximal end of the nail stem by means of the insertion bolt, the alignment pin 6 is placed in hole 20*a* or 18 of the stem 2 and hole 19 or 18 of the fastener 4 (see FIGS. 14A-D, 14F, and 15A-D). The placement of the alignment pin 6 in holes 19 and 20*a* secures the position of the fastener 4 relative to the nail stem 2. The prongs 38 of the alignment pin 6 traverses the width or the diameter of the nail stem 2 (and by default, the fastener 4) so that the grip 30 is flush against one side of the nail stem 2 and the bulbous tip 34*a*, 34*b* extrudes through hole 20*a* on the opposite side of the nail stem 2. During withdrawal of the alignment pin the prongs 38 compress to allow the bulbous tip 34*a*, 34*b* pass through the holes 19 and 20*a*. The force to withdraw the alignment pin is initially high to compress the prongs but then relaxes back to a lower force as the bulbous tip passes through the holes of the nail stem and fastener. The force required to withdraw the alignment pin 6 is controlled by the size of the bulbous tips 34*a/b* relative to holes 19 and 20*a* and can be adapted to produce a higher or lower force as desired.

FIG. 15B illustrates the alignment pin 6 secured in place by holes 19 and 20*a*. The prong 38 of the alignment pin 6 traverses the width or the diameter of the nail stem 2 (and by default, the fastener 4) so that the grip 30 is flush against one side of the nail stem 2 and the bulbous tip 34*a*, 34*b* extrudes through hole 20*a* on the opposite side of the nail stem 2. A more detailed view of section AE/AF of FIG. 15B is illustrated in FIG. 15C/15D, while FIG. 15D illustrates the fastener 4 in place in the system 1 with the alignment pin 6 removed.

The movement of the fastener 4 in the IM nail system 1 during the compression locking mode is illustrated in FIGS. 16A-D and FIGS. 17A-D. Although these figures do not show the locking bolt 40 in situ, the figures illustrate the movement of the fastener 4 as if the locking bolt 40 was advancing into the conduit 22. The locking bolt 40 is not shown there to more clearly illustrate the movement of the fastener 4. As described above, the locking bolt 40 advances into the conduit 22 of the nail stem 2 and the central shaft 22*a* of the fastener 4, until it interfaces against the bone screw 53. In this position, the stop 8 of the fastener 4 is at a proximal end of the hole 20*a* of the nail stem 2, and has yet to engage with the hole 20 of the nail stem 2 (FIGS. 16C and 16D). Further rotation of the locking bolt 40 acts on the proximally-placed bone screw 50 simultaneously with the fastener 4, which pushes the fastener 4 distally by 1-2 mm. The stop 8, being configured to mate with the slot 20*a* at all times, is free to move distally (and in the reverse, proximally) within the confines of the slot 20*a* (see FIGS. 17B, 17C and 17D relative to FIGS. 16B, 16C and 16D, respectively).

Figure 18B:
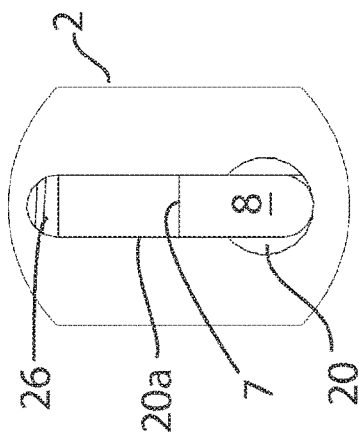
FIGS. 18A-D illustrates the full distal advancement position of the fastener in the IM nail system during the dynamisation locking mode, where the stop of the fastener is resting in a keyhole-type aperture of the nail stem.
Figure 18C:
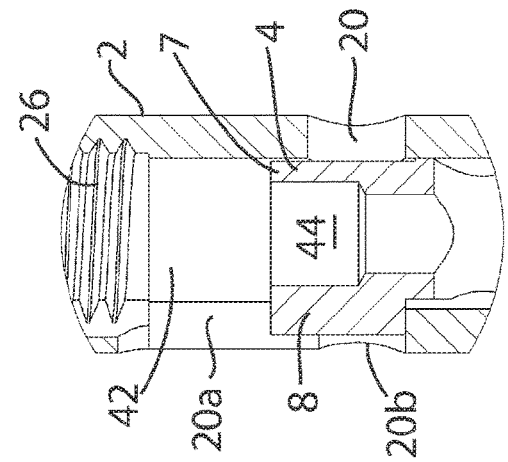
Figure 18D:
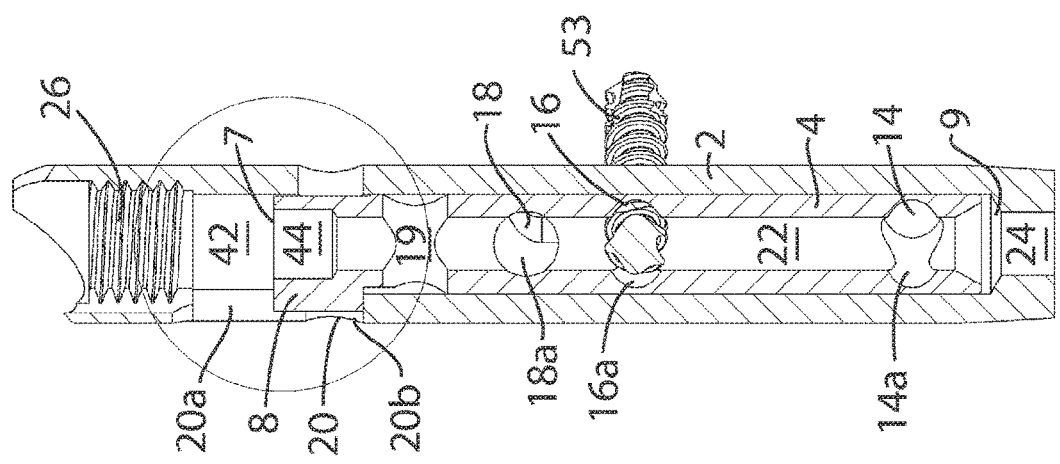
Figure 18A:
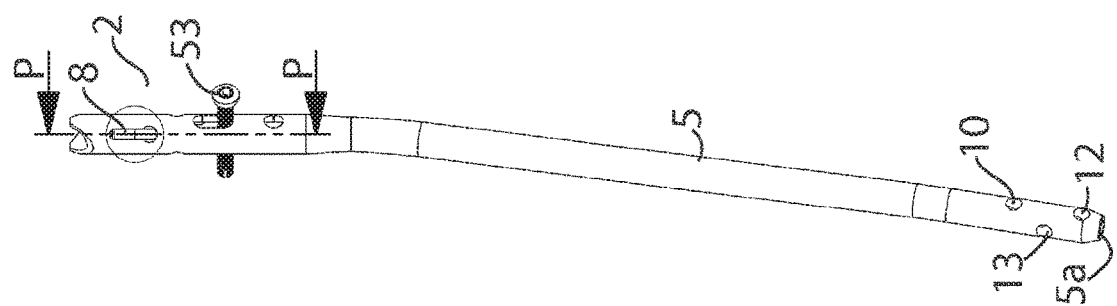

FIGS. 18A-D illustrates the fastener 4 advanced distally in the IM nail system 1 during, for example, the dynamisation locking mode, where the stop 8 of the fastener 4 has engaged with the hole 20 and slot 20*a* of the nail stem 2. By using the slot 20*a* in the nail stem 2 and the aligned hole 19 in the fastener 4, the fastener 4 can advance distally by 5-7 mm for dynamisation locking. FIG. 18B illustrates view Q from FIG. 18A and shows the stop 8 resting against the surface 20B of the hole 20 in the nail stem 2.

Turning now to FIGS. 19A-F, which are also in regard to the storage, transportation and intra-operative attachment of the insertion handle to the proximal end of the nail stem by means of the insertion bolt 100. The alignment pin 6 is placed in hole 20*a* or 18 of the stem 2 and hole 19 or 18 of the fastener 4, as described above for FIGS. 14A-F and 15AF. However, in FIGS. 19A-F, there is an alternative flange 106 presented for the insertion bolt 100, where the flange 106 further comprises a berm 114 sandwiched between the parallel sections 112 and 113, and which encircles the circumference of the flange 106. The berm 114 matingly engages with a converse radial indentation 400 on the proximal end 7 of the fastener 4. Further advancement of the insertion bolt 100 into the nail stem 2 will engage the tapered section 113 of insertion bolt 100 in the proximal end 7 of the fastener 4. This advancement ensures a rigid interference connection between the fastener 4 and the insertion bolt 100. The engagement of the berm 114 and radial indentation 400 further ensures this rigid interference connection. At this point the alignment pin 6 can be withdrawn and the fastener 4 will be held in place relative to the nail stem 2, with no allowed relative movement. The berm and converse radial indentation 400 provide a defined assembly location for the assembly of the insertion bolt 100 to the fastener 4. The assembled force will be consistent, and as the user is tightening the insertion bolt, the user will feel resistance as the insertion bolt 100 advances. This is followed by a reduction in resistance as the berm 114 is located in the indentation 400, indicating that engagement has occurred.

FIG. 20A illustrates a side view of the fastener 4, with the stop 8 facing rearward (away from view). The section along axis AS-AS of the fastener 4 (as illustrated in FIGS. 20B and 20C) shows the stop 8 facing to the right. In this aspect, the proximal end 7 of the fastener 4 further comprises a slit 402 that will facilitate a greater interference fit between the fastener 4 and the insertion bolt 100. As the insertion bolt 100 advances into the proximal end 7 of the fastener 4 and the tapered section 113 engages with the fastener 4, the slit 402 will allow a portion of the hollow central shaft 22*a* of the proximal end 7 of the fastener 4 to expand to accommodate the insertion bolt 100 once the assembly force exceeds the resistance force. This embodiment will allow for a dimensionally tighter interference fit of the component parts and a relatively lower assembly force.

FIG. 20D illustrates a side view of the fastener 4, with the stop 8 facing rearward (away from view). The section along axis AU-AU of the fastener 4 (as illustrated in FIGS. 20E and 20F) shows the stop 8 facing to the right. In this aspect, the fastener 8 is further defined by the radial indentation 400 on the proximal end 7 of the fastener 4. The radial indentation 400 matingly engages with the berm 114 on the insertion bolt 100 to provide a greater interference fit with the insertion bolt 100.

In the specification, the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. An intramedullary nail system (1) comprising a fastener (4) and a nail stem (2), the nail stem (2) having a multi-featured proximal end (3), a distal end (5), and a central conduit (22) configured to accommodate the fastener (4), the fastener (4) having a proximal end (7), a distal end (9), and a central shaft (22*a*), wherein the fastener (4) comprises a stop (8) extending laterally from the proximal end (7) relative to a vertical axis of the fastener (4) and which is configured to matingly engage with an internal wall (3*a*) of the multi-featured proximal end (3), the internal wall (3*a*) further comprising a longitudinal indentation (11) in communication with a first slot (20*a*) and a first hole (20) on the internal wall (3*a*), in which the longitudinal indentation (11) provides clearance for the stop (8) when the fastener (4) is placed within the central conduit (22) and wherein distal movement of the fastener (4) within the nail stem (2) is limited by the engagement of the stop (8) within the dimensions of the first slot (20*a*) and the dimensions of the first hole (20) in the nail stem (2) to provide control over rotational and distal movement of the system (1) when secured with a bone screw.

2. An intramedullary nail system (1) according to claim 1, wherein the stop (8) matingly engages with the first slot (20*a*) to provide variable restraint over rotational and distal movement of the system (1).

3. An intramedullary nail system (1) according to claim 1, wherein the nail stem (2) further comprises a second hole (18), an aperture (14), a second slot (16), and a first micro-slot (14') having a smaller length relative to a length of the second slot (16) configured to accommodate a bone screw.

4. An intramedullary nail system (1) according to claim 3, wherein the nail stem (2) further comprises a second micro-slot (18') having a smaller length relative to a length of the second slot (16); wherein the first micro-slot (14') and the second slot (16) are parallel and share a line of symmetry; and wherein the second micro-slot (18') and the second slot (16) are offset relative to each other.

5. An intramedullary nail system (1) according to claim 1, wherein the fastener (4) further comprises at least one hole (14*a*, 16*a*, 18*a*, 19) configured to accommodate a bone screw.

6. An intramedullary nail system (1) according to claim 3, wherein the fastener (4) further comprises at least one hole (14*a*, 16*a*, 18*a*, 19) configured to accommodate a bone screw and wherein the at least one hole (14*a*) has a smaller diameter relative to a diameter of the aperture (14) or the first micro-slot (14') of the nail stem (2).

7. An intramedullary nail system (1) according to claim 1, further comprising an insertion bolt (100), wherein the insertion bolt (100) comprises a threaded proximal end (102), a conduit (104), and a threaded distal end (108) having a flange (106) extending distally therefrom; wherein the flange (106) comprises a co-axial section (110), a tapered section (113), and a parallel section (112) extending distally from the distal end (108) and configured to engage with the proximal end (7) of the fastener (4); wherein the flange (106)

further comprises a berm (114) that is configured to matingly engage with the proximal end (7) of and presses against the fastener (4); and wherein the berm (114) is sandwiched between the parallel section (112) and the tapered section (113).

8. An intramedullary nail system (1) according to claim 1, further comprising a locking bolt (40) configured to matingly engage with a proximally placed bone screw in the nail stem (2).

9. An intramedullary nail system (1) according to claim 8, wherein the locking bolt (40) comprises a proximal threaded section (46) and a distal straight rod (48) connected thereto, wherein the rod (48) comprises an interface (42) on its distal end (44), which is configured to interact with a proximal bone screw.

10. An intramedullary nail system (1) according to claim 1, in which the placement of a bone screw (50, 52, 53, 54, 56) in a hole (18, 20, 14a, 16a, 18a, 19), a slot (16), a micro-slot (14',18') or an aperture (14) secures the fastener (4) and nail stem (2) in place.

11. An intramedullary nail system (1) according to claim 5, wherein the fastener (4) comprises at least two holes (14a, 16a) configured to accommodate a bone screw, the nail stem (2) further comprises a second hole (18), an aperture (14), at least one a second slot (16), and at least one micro-slot (14' 18') having a smaller length relative to a length of the second slot (16) configured to accommodate a bone screw (50, 52, 53, 54, 56); and wherein placement of two bone screws (50, 52) parallel to each other in each of the at least two holes (14a, 16a) in the fastener (4), the aperture (14), and the second slot (16) provides a locking configuration adapted to mediate controlled axial movement while preserving torsional stability of the system (1).

12. An intramedullary nail system (1) according to claim 5, wherein the nail stem (2) further comprises a second hole (18), an aperture (14), a second slot (16), and at least one micro-slot (14'18') having a smaller length relative to a length of the second slot (16) configured to accommodate a bone screw (50, 52, 53, 54, 56); and wherein placement of a bone screw (50) in the at least one hole (16a) in the fastener (4) and the slot (16) provides a locking configuration adapted to allow controlled axial movement of a proximal bone fragment over a desired range while the system (1) is secured in situ.

13. An intramedullary nail system (1) according to claim 1, further comprising an alignment pin (6) adapted for securing the fastener (4) within the nail stem (2) during transport and use.

14. An intramedullary nail system (1) according to claim 7, further comprising an alignment pin (6) adapted for securing the fastener (4) within the nail stem (2) during transport and use and wherein the insertion bolt (100) is configured to matingly engage with the fastener (4) in the nail stem (2).

15. An intramedullary nail system (1) according to claim 1, the system (1) further comprising an end cap (58) adapted to matingly engage with a threaded portion (26) of the nail stem (2).

16. An intramedullary nail system (1) according to claim 15, wherein rotational movement of the endcap (58) advances the fastener (4) distally against one or more proximally placed bone screws and rigidly locks the system (1) to prevent axial and torsional motion.

17. A kit of parts for use in repairing a bone fracture, the kit comprising an intramedullary nail system (1) comprising a fastener (4) and a nail stem (2), the nail stem having a multi-featured proximal end (3), a distal end (5), and a central conduit (22) configured to accommodate the fastener (4), the fastener (4) having a proximal end (7), a distal end (9) and a central shaft (22a), wherein the fastener (4) comprises a stop (8) extending laterally from the proximal end (7) relative to a vertical axis of the fastener (4) and configured to matingly engage with an internal wall (3a) of the multi-featured proximal end (3), the internal wall (3a) further comprising a longitudinal indentation (11) in communication with a slot (20a) and a hole (20) on the internal wall (3a), in which the longitudinal indentation (11) provides clearance for the stop (8) when the fastener (4) is placed within the central conduit (22) and wherein distal movement of the fastener (4) within the nail stem (2) is limited by the engagement of the stop (8) within the dimensions of the slot (20a) and the dimensions of the hole (20) in the nail stem (2) to provide control over rotational and distal movement of the system (1) when secured with a bone screw.

* * * * *